(12) United States Patent
Heyer et al.

(10) Patent No.: US 6,559,356 B1
(45) Date of Patent: May 6, 2003

(54) NUCLEIC ACID MOLECULES WHICH ENCODE PROTEINS HAVING FRUCTOSYL TRANSFERASE ACTIVITY AND METHODS FOR PRODUCING LONG-CHAIN INULIN

(75) Inventors: Arnd G. Heyer, Berlin (DE); Elke Hellwege, Berlin (DE); Dominique Gritscher, Berlin (DE)

(73) Assignee: Max-Planck-Gesellschaft zur Forderung der Wissenschaften e.V, Berlin (DE)

( * ) Notice: Subject to any disclaimer, the term of this patent is extended or adjusted under 35 U.S.C. 154(b) by 0 days.

(21) Appl. No.: 09/565,264

(22) Filed: May 5, 2000

Related U.S. Application Data

(63) Continuation of application No. PCT/EP98/07115, filed on Nov. 6, 1998.

(30) Foreign Application Priority Data

Nov. 6, 1997 (DE) .......................................... 197 49 122

(51) Int. Cl.[7] .................. C12N 15/29; C12N 15/54; C12N 15/82; A01H 5/00; C12P 19/04
(52) U.S. Cl. .................... 800/284; 800/278; 800/287; 800/306; 800/312; 800/317.2; 800/317.4; 800/320; 800/320.1; 800/320.2; 800/320.3; 435/69.1; 435/101; 435/193; 435/320.1; 435/419; 536/23.6
(58) Field of Search ................ 536/23.6; 435/69.1, 435/101, 193, 320.1, 419; 800/278, 284, 287, 320.2, 320.1, 317.2, 317.4, 320.3, 320, 306, 312

(56) References Cited

U.S. PATENT DOCUMENTS 5,576,428 A * 11/1996 Butler et al. ................ 536/24.1

FOREIGN PATENT DOCUMENTS

| AU | 199727741 | 11/1997 |
| DE | 196 17 687 A1 | 11/1996 |
| EP | 0 627 490 A1 | 12/1994 |
| WO | WO 94/14970 | 7/1994 |
| WO | WO 96/21023 | 7/1996 |

OTHER PUBLICATIONS

Goblet et al. Genbank Accession No. U 84398, Jan. 1997.*
Elke M. Hellwege, et al., "Differences in Chain Length Distribution of Inulin from *Cynara scolymus* and *Helianthus tuberosus* are Reflected in a Transient Plant Expression System Using the Respective 1–FFT cDNAs," *FEBS Letters*, 427, pp. 25–28 (1998).
Elke M. Hellwege et al., "Transgenic Potato Tubers Accumulate High Levels of 1–Kestose and Nystose: Functional Identification of a Sucrose 1–Fructosyltransferase of Artichoke (*Cynara scolymus*) Blossom Discs," *The Plant Journal*, 12(5), pp. 1057–1065 (1997).
Andries J. Koops, et al., "Purification and Characterization of the Enzymes of Fructan Biosynthesis in Tubers of *Helianthus tuberosus* 'Colombia' 1. Fructan:Fructan Fructosyl Transferase," *Journal of Experimental Botany*, 45, pp. 1623–1631 (1994).
Marcel Lüscher et al., "Inulin Synthesis by a Combination of Purified Fructosyltransferases from Tubers of *Helianthus tuberosus*," *FEBS Letters*, 385, pp. 39–42 (1996).
Ingrid M. van der Meer et al., "Cloning of the Fructan Biosynthesis Pathway of Jerusalem Artichoke", *The Plant Journal*, 15(4), pp. 489–500 (1998).

* cited by examiner

Primary Examiner—David T. Fox
(74) Attorney, Agent, or Firm—Fish & Neave; James F. Haley, Jr.; Karen E. Brown

(57) ABSTRACT

Nucleic acid molecules which encode proteins having fructosyl transferase activity and methods for producing long-chain inulin Nucleic acid molecules are described encoding proteins with the enzymatic activity of a fructosyl transferase. These enzymes are fructosyl transferases (FFT). Moreover, vectors and host cells are described containing the nucleic acid molecules of the invention, in particular transformed plant cells, plant tissue and plants regenerable therefrom, which express the described FFT. Furthermore, methods for the production of long-chain inulin by using the described proteins, hosts, in particular the plant cells and/or FFT produced by them, are described.

29 Claims, 5 Drawing Sheets

NUCLEIC ACID MOLECULES WHICH ENCODE PROTEINS HAVING FRUCTOSYL TRANSFERASE ACTIVITY AND METHODS FOR PRODUCING LONG-CHAIN INULIN

CROSS-REFERENCE TO RELATED APPLICATION

This application is a continuation of international application PCT/EP98/07115, filed Nov. 6, 1998, which designated the United States.

BACKGROUND OF THE INVENTION

The present invention relates to nucleic acid molecules encoding proteins with the enzymatic activity of a fructosyl transferase (FFT). The invention also relates to vectors containing such nucleic acid molecules as well as to host cells transformed with said nucleic acid molecules, in particular plant cells, plant tissue and plants. Moreover, methods for the production of transgenic plants are described which synthesize long-chain inulin due to the introduction of nucleic acid molecules encoding an FFT. The present invention also relates to methods of producing FFT and to the production of long-chain inulin in various host organisms, in particular plants, as well as to in vitro methods for producing long-chain inulin by means of the FFT of the invention. The present invention further relates to the host cells of the invention and to the inulin obtainable by the processes of the present invention.

Water-soluble, linear polymers allow for a variety of applications, for example for increasing the viscosity in aqueous systems, as detergents, as suspending agents or for speeding up sedimentation, for complexing and, however, also for binding water. Polymers which are based on saccharides, such as fructosyl polysaccharides, are particularly interesting raw materials as they are biodegradable. Apart from their application as regenerable raw materials for the industrial production and processing, fructosyl polymers are also to be considered as additives in foodstuffs, for example as sweeteners. For various uses, polymers with varying chain-lengths are needed. Whereas short- and medium-chain polymers are particularly preferred in the food processing industry, polymers with a high degree of polymerization (DP) are needed for technical uses, such as the production of surfactants.

So far only methods for producing long-chain fructan polysaccharides in plants have been described in which fructosyl transferases of bacterial origin are expressed. Most bacterial fructosyl transferases synthesize levan, a β-2,6 linked fructosyl polymer which has numerous β-2,1-branchings. Due to its numerous branchings levan has decisive disadvantages when it comes to technical processing and is therefore considerably less significant as a technical raw material then inulin. Up to now, only one bacterial gene is known, the gene product of which is involved in the synthesis of inulin, namely the ftf gene from *Streptococcus mutans*. It is in principle possible to express the gene in plants if the gene has previously been genetically engineered. However, the inulin yield obtained from transgenic plants is so low that the economic utilization of the transgenic plants is out of question.

Furthermore, a method for producing transgenic plants expressing fructosyl transferases from *Helianthus tuberosus* is known. The expression of these genes in transgenic plants leads to the production of inulin with an average degree of polymerization of DP=6 to DP=10. Polymers with this degree of polymerization may not be referred to as long-chain inulin. Inulin with an average DP=6 to DP=10 is unsuitable for most technical uses.

Methods for an economic production of long-chain inulin in plants or for synthesizing enzymes for the production of long-chain inulin are not known.

PCT/US89/02729 describes the possibility of synthesizing carbohydrate polymers, in particular dextran or polyfructose, in transgenic plant cells, specifically in the fruits of transgenic plants. In order to produce plants modified in such a way, the use of levan sucrases from microorganisms, in particular from *Aerobacter levanicum*, *Streptococcus salivarius* and *Bacillus subtilis*, or of dextran sucrases from *Leuconostoc mesenteroides* is proposed. Neither the formation of the active enzymes nor that of levan or dextran or the production of transgenic plants is described. PCT/EP93/02110 discloses a method for producing transgenic plants expressing the Isc gene of the levan sucrase from the gram-negative bacterium *Erwinia amylovora*. The plants produce a high-molecular, strongly branched levan. PCT/NL93/00279 describes the transformation of plants with chimeric genes containing the sacB gene from *Bacillus subtilis* or the ftf gene from *Streptococcus mutans*. Transgenic plants expressing the sacB gene produce a branched levan. Plants expressing the ftf gene synthesize high-molecular inulin; the yield, however, is so low that an economic utilization is out of question. PCT/NL96/00012 discloses DNA sequences encoding enzymes synthesizing carbohydrate polymers as well as the production of transgenic plants by means of these DNA sequences. The disclosed sequences are derived from *Helianthus tuberosus*. According to PCT/NL96/00012, the disclosed sequences may be used in order to modify the fructan profile of petunia and potato, but also of *Helianthus tuberosus* itself. When expressing the SST and the FFT gene in transgenic plants, it is possible to produce inulin. The average degree of polymerization of inulin, however, ranges between DP=6 and DP=10. The production of high-molecular inulin is not possible by means of the method described in PCT/NL96/00012. PCT/EP97/02195 describes a method for producing transgenic, inulin-producing plants by means of the ftf gene from *Streptococcus mutans*. The yield of high-molecular inulin is low, as is the case with the plants described in PCT/NL9300279. DE 197 08 774.4 describes the production of short-chain inulin by means of enzymes exhibiting fructosyl polymerase activity. The short-chain inulin may be produced in transgenic plants. The yield of short-chain inuin is high and in potato it corresponds to the cellular content of sucrose. The production of long-chain inulin, however, is not described.

The synthesis of inulin in plants has been thoroughly examined (Pollock & Chafterton, Fructans, The Biochemistry of Plants Vol. 14 (1988), Academic Press, pp.109-140). However, the inulin occurring naturally in plants is short-chain fructan with a maximum degree of polymerization of approximately DP=35 (Pollock & Chatterton, 1988, loc.cit.). Synthesis and metabolism of fructans in plants are based on the activity of at least three enzymes: a sucrose-dependent sucrose-fructosyl transferase (SST) forming the trisaccharide kestose, a fructan-dependent fructan-fructosyl transferase (FFT) which transfers fructosyl residues from fructan molecules with a minimum degree of polymerization of DP=3 (kestose) to sucrose and higher fructans, and a fructan exohydrolase (FEH) which removes fructose residues from fructan molecules. It is not known whether differences in the average molecular weight of the inulin in various plant species, for example about $2\times10^3$ in the case of *Allium cepa* and $5\times10^3$ in the case of *Helianthus tuberosus*, are based on the different properties of their SST, FFT or FEH.

For this reason it is not possible in view of the present knowledge relating to the inulin synthesis in plants to identify suitable DNA sequences by means of which high-molecular inulin might be synthesized in plants in economically interesting amounts.

Thus, the technical problem underlying the present invention is to provide nucleic acid molecules and methods which allow for the production of genetically modified organisms, in particular plants, capable of forming long-chain inulin.

This problem is solved by the provision of the embodiments characterized in the claims.

SUMMARY OF THE INVENTION

Therefore, the present invention relates to nucleic acid molecules encoding proteins with the enzymatic activity of an FFT, selected from the group consisting of
(a) nucleic acid molecules encoding a protein comprising the amino acid sequence indicated under SEQ ID NO: 2 or SEQ ID NO: 4;
(b) nucleic acid molecules comprising the nucleotide sequence indicated under SEQ ID NO: 1 or SEQ ID NO: 3 or a corresponding ribonucleotide sequence;
(c) nucleic acid molecules which hybridize to a complementary strand of the nucleic acid molecules mentioned under (a) or (b) under stringent conditions; and
(d) nucleic acid molecules comprising a fragment of the nucleotide sequence of (a), (b) or (c).

In the context of the present invention a fructosyl transferase (FFT) is a protein capable of catalyzing the formation of β-2,1-glycosidic and/or β-2,6-glycosidic bonds between fructose units. Thereby, a fructosyl residue to be transferred may be derived from 1-kestose or from a fructan polymer. In connection with the present invention, a high-molecular fructan is a polymer the molecules of which contain an average number of more than 20, preferably more than 25 and even more preferably at least 32 fructosyl residues. Furthermore, the high-molecular fructan is preferably a polymer the molecules of which contain on the average less than 3000, more preferably less than 300 and particularly preferred less than 100 fructosyl residues. The fructosyl residues may be either glycosidically linked by β-2,1 bonds or by β-2,6 bonds. In the case of inulin the residues are generally linked by β-2,1 glycosidic bonds. To a low degree, also β-2,6-bonds may occur, in particular by less than 5%, preferably by less than 3%, more preferably by less than 1.5% and most preferably by less than 0.5%. The fructosyl polymer may carry at its end a glucose residue which is linked via the C-1 OH-group of the glucose and the C-2 OH-group of a fructosyl residue. In this case, a sucrose molecule is also contained in the fructosyl polymer.

Surprisingly, high amounts of high-molecular inulin are formed during the expression of the nucleic acid molecules of the invention in transformed plants. The inulin formed in the plants exhibits an average degree of polymerization of clearly more than DP=20. This was unexpected since a similar enzyme from *Helianthus tuberosus* is involved in the synthesis of inulin with an average degree of polymerization of less than DP=20 in transgenic plants (PCT/NL96/00012).

The nucleic acid molecules of the invention may be DNA as well as RNA molecules. Corresponding DNA molecules are for example genomic DNA or cDNA molecules. The nucleic acid molecules of the invention may be isolated from natural sources, preferably from artichoke, or they may be synthesized according to known methods. By means of conventional molecular-biological techniques it is possible (see e.g. Sambrook et al., 1989, Molecular Cloning, A Laboratory Manual, $2^{nd}$ edition, Cold Spring Harbor Laboratory Press, Cold Spring Harbor, N.Y.) to introduce various mutations into the nucleic acid molecules of the invention, which leads to the synthesis of proteins with probably modified biological properties. In this respect, it is possible on the one hand to produce deletion mutants, in which nucleic acid molecules are produced by progressing deletions at the 5' or 3' end of the coding DNA sequence. These nucleic acid molecules lead to the synthesis, of correspondingly shortened proteins. By means of such deletions at the 5' end of the nucleotide sequence it is for example possible to identify amino acid sequences which are responsible for the translocation of the enzyme into the vacuole (transit peptides). This allows for the targeted production of enzymes which, due to the removal of the corresponding sequences, are no longer located within the vacuole but within the cytosol, or within other compartments due to the addition of other signal sequences.

On the other hand, it is also conceivable to introduce point mutations at positions in which a modification of the amino acid sequence for example influences the enzyme activity or the regulation of the enzyme. In this manner e.g. mutants may be produced which exhibit a modified $K_m$ value or which are no longer subject to the regulation mechanisms occurring in the cell, such as allosteric regulation or covalent modification.

Furthermore, mutants may be produced which exhibit a modified substrate or product specificity. Furthermore, mutants with a modified activity-temperature-profile may be produced.

For recombinant DNA manipulation in prokaryotic cells, the nucleic acid molecules of the invention or parts of these molecules may be inserted into plasmids which allow for a mutagenesis or a sequence modification by recombination of DNA sequences. By means of standard techniques (cf. Sambrook et al., 1989, Molecular Cloning: A laboratory manual, $2^{nd}$ edition, Cold Spring Harbor Laboratory Press, N.Y., USA) base exchanges may be carried out or natural or synthetic sequences may be added. In order to link the DNA fragments to each other, adapters or linkers may be connected with the fragments. Furthermore, manipulations may be used which provide suitable restriction sites or which remove superfluous DNA or restriction sites. If use can be made of insertions, deletions or substitutions, in vitro mutagenesis, primer repair, restriction or ligation may be used. As analyzing method, use is usually made of sequence analysis, restriction analysis or further biochemico-molecular-biological methods.

In the context of the present invention the term "hybridization" means hybridization under conventional conditions, preferably under stringent conditions, as described for example in Sambrook et al., Molecular Cloning, A Laboratory Manual, $2^{nd}$ edition (1989), Cold Spring Harbor Laboratory Press, Cold Spring Harbor, N.Y. An example for stringent hybridization conditions is a hybridization in 50% formamide, 5×SSC, 5×Denhardt's solution, 40 mM sodium phosphate pH 6.8; 0.5% (w/v) BSA, 1% (w/v) SDS, 0.1 mg/ml herring sperm DNA at 42° C. An example for conventional non-stringent hybridization conditions is a hybridization under the above-described conditions in which, however, 30% formamide is used instead of 50%. Washing conditions in the case of stringent conditions are preferably 0.5×SSC/0.5% SDS at 60° C. and in the case of non-stringent conditions preferably 2×SSC/0.5% SDS at 56° C.

Nucleic acid molecules which hybridize to the molecules of the invention can e.g. be isolated from genomic or from cDNA libraries produced from corresponding organisms, such as artichoke.

Such nucleic acid molecules may be identified and isolated by using the molecules of the invention or parts of these molecules or, as the case may be, the reverse complements of these molecules, e.g. by hybridization according to standard techniques (see e.g. Sambrook et al., 1989, Molecular Cloning, A Laboratory Manual, $2^{nd}$ edition, Cold Spring Harbor Laboratory Press, Cold Spring Harbor, N.Y.). As a hybridization probe e.g. nucleic acid molecules may be used which exhibit exactly or basically the nucleotide sequence indicated under SEQ ID No. 1 or SEQ ID No. 3 or parts thereof. The fragments used as hybridization probe may also be synthetic fragments produced by means of the usual synthesis techniques and the sequence of which is basically similar to that of a nucleic acid molecule of the invention.

The molecules hybridizing to the nucleic acid molecules of the invention also comprise fragments, derivatives and allelic variants of the above-described nucleic acid molecules encoding a protein of the invention. "Fragments" are supposed to be parts of the nucleic acid molecules which are long enough in order to encode a protein of the invention. In this context, the term "derivative" means that the sequences of these molecules differ from the sequences of the above-described nucleic acid molecules at one or more positions. However, they exhibit a high degree of homology to these sequences. Homology means a sequence identity of at least 40%, in particular an identity of at least 60%, preferably of more than 80% and most preferably of more than 90%. The proteins encoded by these nucleic acid molecules exhibit a sequence identity to the amino acid sequence indicated under SEQ ID No. 2 of at least 80%, preferably 85% and particularly preferred of more than 90%, more preferred of more than 95%, even more preferred of more than 97% and most preferred of more than 99%. The deviations from the above-described nucleic acid molecules may, for example, result from deletion, substitution, insertion and/or recombination.

The nucleic acid molecules which are homologous to the above-described molecules and represent derivatives of these molecules, are usually variations of these molecules representing modifications with the same biological function. These may be naturally occurring variations, for example sequences from other organisms, or mutations, whereby these mutations may have occurred naturally or they may have been introduced by means of targeted mutagenesis. Furthermore, the variations may be synthetically produced sequences. The allelic variants may either be naturally occurring variants or synthetically or recombinantly produced variants. The proteins encoded by the various variants of the nucleic acid molecules of the invention exhibit certain common characteristics such as the enzyme activity, molecular weight, immunological reactivity or conformation or physical properties such as the mobility in gel electrophoresis, chromatographic characteristics, sedimentation coefficients, solubility, spectroscopic properties, stability, pH-optimum, temperature-optimum etc.

In a preferred embodiment the nucleic acid sequences of the invention are derived from artichoke (*Cynara scolymus*).

The invention further relates to vectors containing the nucleic acid molecules of the invention. These are preferably plasmids, cosmids, viruses, bacteriophages and other vectors common in gene technology.

Within the vector of the invention the nucleic acid molecule of the invention is preferably operably linked to regulatory elements which ensure the transcription and synthesis of a translatable RNA in prokaryotic and/or eukaryotic cells.

The expression vectors of the invention allow for the production of long-chain inulin in various host organisms, in particular in prokaryotic or eukaryotic cells such as bacteria, fungi, algae, animal cells and preferably plant cells and plants. Preferred host organisms are in particular yeasts such as e.g. *S. cerevisiae*, and lactic acid bacteria such as *Streptococcus thermophilus, Lactobacillus bulgaricus, Streptococcus lactis, S. cremoris, Lactobacillus acidophilus* and *Leuconostoc cremoris*. The encoded enzymes may probably also be used outside of the host organisms for the production of long-chain inulin. Plant cells are particularly preferred.

A survey concerning various expression systems may be found e.g. in Methods in Enzymology 153 (1987), 385–516, in Bitter et al. (Methods in Enzymology 153 (1987), 516–544), Sawers et al., Applied Microbiology and Biotechnology 46 (1996), 1–9, Billmann-Jacobe, Current Opinion in Biotechnology 7 (1996), 500–504, Hockney, Trends in Biotechnology 12 (1994), 456–463, and Griffiths et al., Methods in Molecular Biology 75 (1997), 427–440. Expression systems for yeast have been described in Hensing et al., Antonie van Leuwenhoek 67 (1995), 261–279, Bussineau et al., Developments in Biological Standardization 83 (1994), 13–19, Gellissen et al., Antonie van Leuwenhoek 62 (1992), 79–93, Fleer, Current Opinion in Biotechnology 3 (1992), 486–496, Vedvick, Current Opinion in Biotechnology 2 (1991), 742–745, and in Buckholz, Bio/Technology 9 (1991), 1067–1072. Expression vectors have been described to a great extent in the prior art. Apart from a selection marker gene and a replication origin ensuring replication in the selected host, they usually contain a bacterial or viral promoter and in most cases a termination signal for transcription. There is at least one restriction site or one polylinker between the promoter and the termination signal which allows to insert a coding DNA sequence. If it is active in the selected host organism, the DNA sequence naturally controlling the transcription of the corresponding gene may be used as promoter sequence. This sequence may also be exchanged with other promoter sequences. Use may also be made of promoters which lead to a constitutive expression of the gene as well as of inducible promoters allowing for a targeted regulation of the expression of the downstream gene. Bacterial and viral promoter sequences with these properties have been extensively described in the prior art. Regulatory sequences for the expression in microorganisms (such as *E. coli, S. cerevisiae*) have been sufficiently described in the prior art. Promoters which allow for a particularly strong expression of the downstream gene are e.g. the T7 promoter (Studier et al., Methods in Enzymology 185 (1990), 60–89), lacuv5, trp, trp-lacUV5 (DeBoer et al., in Rodriguez and Chamberlin (eds.), Promoters, Structure and Function; Praeger, New York (1982), 462–481; DeBoer et al., Proc. Natl. Acad. Sci. USA (1983), 21–25), λp1, rac (Boros et al., Gene 42 (1986), 97–100). Usually, the amounts of protein are highest from the middle towards the end of the logarithmic phase of the microorganisms' growth cycle. For this reason, inducible promoters are preferably used for the synthesis of proteins. These frequently lead to higher protein yields than constitutive promoters. The use of strongly constitutive promoters often leads, via the permanent transcription and translation of the cloned gene, to the loss of energy for other essential cell functions, which slows down the growth of the cell (Bernard R. Glick, Jack J. Pasternak, Molekulare Biotechnologie (1995), Spektrum Akademischer Verlag GmbH, Heidelberg Berlin Oxford, p. 342).

Thus, in order to reach an optimum amount of protein a two-stage process is often used. At first, host cells are cultivated under optimum conditions until a relatively high cell density is achieved. In the second stage, transcription is induced depending on the kind of promoter used. In this context, a tac-promoter inducible by lactose or IPTG (=isopropyl-β-D-thiogalacto-pyranosid) is particularly suitable (deBoer et al., Proc. Natl. Acad. Sci. USA 80 (1983), 21–25). Termination signals for the transcription are also described in the prior art.

The transformation of the host cell with the corresponding protein-encoding DNA may generally be carried out by means of standard techniques, such as described by Sambrook et al. (Molecular Cloning: A Laboratory Course Manual, $2^{nd}$ edition (1989), Cold Spring Harbor Press, New York). The cultivation of the host cell takes place in nutrient media which correspond to the respective requirements of the host cells used, particularly considering the pH value, temperature, salt concentration, airing, antibiotics, vitamins, trace elements etc.

The purification of the enzyme produced by the host cells may be carried out by means of conventional purification techniques such as precipitation, ion exchange chromatography, affinity chromatography, gel filtration, HPLC reverse phase chromatography etc.

By modifying the DNA expressed in the host cells, a polypeptide may be produced in the host cell which can easier be isolated from the culture medium due to certain properties. Thus, there is the possibility of expressing the protein to be expressed as a fusion protein with a further polypeptide sequence, the specific binding properties of which allow for the isolation of the fusion protein via affinity chromatography (e.g. Hopp et al., Bio/Technology 6 (1988), 1204–1210; Sassenfeld, Trends Biotechnol. 8 (1990), 88–93).

For expression in plant cells, regulatory elements of the patatin B33 promoter are preferred. Other preferred promoters are the 35S CaMV promoter and the promoter of the alcohol dehydrogenase gene from Saccharomyces cerevisiae.

The vectors of the invention may possess further functional units which stabilize the vector within a host organism, e.g. a bacterial replication origin or the 2-micron-DNA for stabilization in Saccharomyces cerevisiae. Furthermore, they may contain left and right border sequences of agrobacterial T-DNA, thus enabling a stable integration into the genome of plants.

The vectors of the invention may further contain functional terminators, such as the terminator of the octopin synthase gene from Agrobacteria.

In another embodiment the nucleic acid molecule of the invention is linked to a nucleic acid molecule within the vector of the invention, said nucleic acid molecule encoding a functional signal sequence in order to direct the enzyme to various cell compartments. This modification may for example consist in an addition of an N-terminal signal sequence for the secretion into the apoplast of higher plants; however, any other modification leading to the fusion of a signal sequence to the encoded FFT is also a subject matter of the invention. The nucleic acid molecule contained in the vector of the invention may in particular contain a sequence encoding an amino acid sequence causing secretion. In this context, use is preferably made of the signal peptide of the α-CGTase from *Klebsiella oxytoca* M5A1 (Fiedler et al., J. Mol. Biol. 256 (1996), 279–291) or of a signal peptide as it is encoded by the nucleotides 11529–11618 of the sequence with the gene bank accession number X 86014.

In a particularly preferred embodiment the invention relates to plasmids p35-csFFT and p33-csFFT, the construction of which is described in the examples (FIG. 2 and 4).

In a further embodiment the invention relates to host cells, which transiently or stably contain the nucleic acid molecules or vectors of the invention or are derived from such cells. In this context, a host cell is an organism capable of taking up recombined DNA in vitro and, if applicable, of synthesizing the proteins encoded by the nucleic acid molecules of the invention. The host cells may be prokaryotic as well as eukaryotic cells. They may in particular be microorganisms. In the context of the present invention, these are all bacteria and protists (such as fungi, in particular yeasts and algae) as they are defined e.g. in Schlegel "Allgemeine Mikrobiologie" (Georg Thieme Verlag (1985), 1–2). In connection with prokaryotic host organisms it should be noted that the positive influence of inulin on the growth of certain microorganisms, such as Bifido bacteria, of the human intestinal tract has successfully been shown. Bifido bacteria have been ascribed a healthy effect (see e.g. Gibson et al., Int. Sugar J. 96 (1994), 381-386; Roberfroid et al., J. of Nutrition 128 (1998), 11–19). A tumor-inhibiting effect has also been discussed (see e.g. Reddy et al, Carcinogenesis 18 (1997), 1371–1374; Singh et al., Carcinogenesis 18 (1997), 833–841). For this reason, the host cells of the invention such as yeast (bread) or lactic acid bacteria (yogurt, butter-milk etc.) are suitable for use in the food processing industry.

In a particularly preferred embodiment a host cell of the invention additionally contains a gene encoding a sucrose-dependent sucrose fructosyl transferase (SST). Such sequences were, for example, isolated from artichoke (German patent application DE-A1 197 08 774), Cichorium intibus (de Halleux et al., Plant Physiol. 113 (1997), 1003–1013), Helianthus tuberosus (WO 96/21023) and Allium cepa (Vijn et al., Plant Physiol. 117 (1998), 1507–1513).

The invention in particular relates to transgenic plant cells transformed with a nucleic acid molecule of the invention or containing the vector systems of the invention or derivatives or parts thereof. These are capable of synthesizing enzymes for the production of long-chain inulin due to the introduction of the vector systems of the invention, derivatives or parts of the vector system. The cells of the invention are preferably characterized in that the introduced nucleic acid molecule of the invention is either heterologous with respect to the transformed cell, i.e. it does not naturally occur in these cells or is localized at a different position within the genome than the respective naturally occurring sequence. Moreover, such a transgenic plant cell of the invention preferably contains a DNA sequence encoding a SST.

The present invention further relates to proteins encoded by the nucleic acid molecules of the invention, as well as to methods for their production wherein the host cell of the invention is cultivated under conditions which allow for the synthesis of the protein. The protein is subsequently isolated from the cultivated cells and/or from the culture medium. The invention further relates to an FFT obtainable from the host cell of the invention or by a method of the invention.

The invention further relates to nucleic acid molecules which specifically hybridize to a nucleic acid molecule of the invention, to a molecule complementary thereto or to a part of such molecules. These are preferably oligonucleotides with a length of at least 10, in particular of at least 15 and particularly preferred of at least 50 nucleotides. The oligonucleotides of the invention may for example be used as primers for a PCR reaction. They may also be components of antisense constructs or of DNA molecules encoding suitable ribozymes.

The present invention also relates to a method for the production of transgenic plant cells, plant tissue and plants comprising the introduction of a nucleic acid molecule or vector of the invention into plant cells, plant tissue and plants. By providing the nucleic acid molecules of the invention it is possible by means of recombinant DNA techniques to produce long-chain inulin in various organisms, in particular in plants, as it was so far impossible by means of conventional, e.g. breeding methods. By increasing the activity of the FFT of the invention, for example by overexpressing the nucleic acid molecules of the invention, or by providing mutants that are no longer subject to cell-specific regulation mechanisms and/or exhibit distinct temperature dependencies with respect to their activity, it is possible to increase the yield of plants correspondingly modified by means of recombinant DNA techniques.

Thus, it is possible to express the nucleic acid molecules of the invention in plant cells in order to increase the activity of the corresponding FFT, or to introduce it into cells that do not normally express this enzyme. It is furthermore possible to modify the nucleic acid molecules of the invention according to methods known to the skilled person, in order to obtain the FFTs of the invention that are no longer subject to cell-specific regulation mechanisms or which exhibit modified temperature-dependencies, substrate or product specificities.

For this purpose, the skilled person may utilize various plant transformation systems. Thus, the use of T-DNA for transforming plant cells has been intensely examined and described in EP-A-120 516; Hoekema: The Binary Plant Vector System, Offsetdrukkerij Kanters B. V., Alblasserdam (1985), Chapter V, Fraley, Crit. Rev. Plant. Sci., 4, 1–46 and An, EMBO J. 4 (1985), 277–287.

For transferring the DNA into the plant cells, plant explants may suitably be co-cultivated with Agrobacterium tumefaciens or Agrobacterium rhizogenes. From the infected plant material (e.g. pieces of leaves, stem segments, roots, but also protoplasts or suspension-cultivated plant cells) whole plants may then be regenerated in a suitable medium which may contain antibiotics or biozides for the selection of transformed cells. The plants obtained in such a way may then be examined as to whether the introduced DNA is present or not. Other possibilities in order to introduce foreign DNA by using the biolistic method or by transforming protoplasts are known to the skilled person (cf. e.g. Willmitzer, L., 1993 Transgenic plants. In: Biotechnology, A Multi-Volume Comprehensive Treatise (H. J. Rehm, G. Reed, A. Pühler, P. Stadler, editors), Vol. 2, 627–659, VCH Weinheim-New York-Basel-Cambridge).

Alternative Systems for the transformation of monocotyledonous plants are the transformation by means of the biolistic approach, the electrically or chemically induced uptake of DNA into protoplasts, the electroporation of partially permeabilized cells, the macro-injection of DNA into inflorescences, the micro-injection of DNA into microspores and pro-embryos by means of swelling (see e.g. Lusardi, Plant J. 5 (1994), 571–582; Paszkowski, Biotechnology 24 (1992), 387–392). Whereas the transformation of dicotyledonous plants by Ti-plasmid-vector systems by means of *Agrobacterium tumefaciens* is a well-established method, more recent studies indicate that the transformation with vectors based on Agrobacterium can also be used in the case of monocotyledonous plants (Chan et al., Plant Mol. Biol. 22 (1993), 491–506; Hiei et al., Plant J. 6 (1994), 271–282; Bytebier et al., Proc. Natl. Acad. Sci. USA 84 (1987), 5345–5349; Raineri et al., Bio/Technology 8 (1990), 33–38; Gould et al., Plant Physiol. 95 (1991), 426–434; Mooney et al., Plant, Cell Tiss. & Org. Cult. 25 (1991), 209–218; Li et al., Plant Mol. Biol. 20 (1992), 1037–1048).

Three of the above-mentioned transformation systems have in the past been established for various types of cereals: electroporation of plant tissue, transformation of protoplasts and the DNA-transfer by particle-bombardment into regenerable tissue and cells (review given in: Jahne et al., Euphytica 85 (1995), 35–44). In the corresponding literature the transformation of wheat is described in various ways (reviewed in Maheshwari et al., Critical Reviews in Plant Science 14 (2) (1995), 149–178).

When expressing the nucleic acid molecules of the invention in plants it is in principle possible that the synthesized protein may be localized within any desired compartment of the plant cell. In order to achieve the localization in a particular compartment the sequence ensuring the localization within the vacuole must be deleted and the remaining coding region has, optionally, to be linked to DNA sequences which ensure the localization within the respective compartment. Such sequences are known in the art (see for example Braun, EMBO J. 11 (1992), 3219–3227; Wolter, Proc. Natl. Acad. Sci. USA 85 (1988), 846–850; Sonnewald, Plant J. 1 (1991), 95–106; Rocha-Sosa, EMBO J. 8 (1989), 23–29).

The present invention also relates to transgenic plant cells, plant tissue and plants which were transformed with one or several of the nucleic acid molecules of the invention, as well as to transgenic plant cells derived from cells transformed in such a way. Such cells contain one or several of the nucleic acid molecules of the invention, whereby this/these is/are preferably linked to regulatory DNA elements that ensure transcription in plant cells, in particular with a promoter. Such cells differ from naturally occurring plant cells in that they contain at least one nucleic acid molecule of the invention which does not naturally occur in these cells or in that such a molecule is integrated at a position within the genome of the cell where it does not naturally occur, i.e. in another genomic environment. Since 1-kestose is the natural substrate of FFT and is itself formed in the reaction of a sucrose-dependent sucrose fructosyl transferase (SST) with the sucrose, it is particularly advantageous and probably necessary to provide an SST apart from the nucleic acid molecule, vector or FFT of the invention. Thus, in a preferred embodiment the present invention relates to transgenic plant cells, plant tissue or plants which additionally contain a gene encoding a sucrose-dependent sucrose fructosyl transferase (SST). These may for example be plants or plant cells which already naturally express an SST such as chicory, Helianthus tuberosus, or dahlia or plants into which an SST-encoding DNA sequence was introduced by means of recombinant DNA techniques. Said sequence may have been introduced independently or simultaneously with a nucleic acid molecule or vector of the invention.

The transgenic plant cells and plant tissues can be regenerated to whole plants by means of techniques known to the skilled person. The plants obtainable by regenerating the transgenic plant cells of the invention are also a subject matter of the present invention. A further subject matter of the invention are plants which contain the above-described transgenic plant cells. The transgenic plant cells may in principle be any desired kind of plant species, i.e. monocotyledonous as well as dicotyledonous plants. They are preferably useful plants, in particular sucrose-containing plants such as rice, maize, sugar beet, sugar cane or potato, vegetable plants (e.g. tomato, carrot, leek, chicory etc.), feeding or pasture grass, sweet potato, wheat, barley, rape or soy bean.

The invention also relates to propagation material and harvest products of the plants of the invention such a fruits, seeds, tubers, rootstocks, seedlings, cutting, calli, cell cultures etc.

A further subject matter of the invention is the long-chain inulin obtainable from the host cells of the invention, in particular from transgenic plant cells, plant tissues, plants as well as from the propagation material and from the harvest products.

In another embodiment the invention relates to methods for producing long-chain inulin comprising:
(a) cultivating a host cell, particularly a plant cell, plant tissue or a plant of the invention, under conditions which allow for the production of FFT and the conversion of 1-kestose, optionally supplied from the outside, or of an equivalent substrate into long-chain inulin; and
(b) recovering the thus produced inulin from the cultivated host cells, in particular plant cells, tissues or plants, or from the medium.

In a further embodiment the invention relates to a method for the production of long-chain inulin comprising:
(a) bringing 1-kestose or an equivalent substrate into contact with an FFT of the invention under conditions which allow for the conversion into long-chain inulin; and
(b) recovering the thus produced inulin.

The recovering of the inulin from various sources, in particular from plant tissue, has for example been described in Gibson et al., Int. Sugar J. 96 (1994), 381–386; Baxa, Czech J. Food Sci. 16 (1998), 72–76; EP-A-787 745; De Leenheer, Carbohydr. Org. Raw Mater. III, Workshop (1996), Meeting Date 1994, 67–92, Verlag VCH Weinheim, Germany and Russian patent RU 2001621 C1.

The present invention further relates to an in vitro method for producing long-chain inulin by using the substrate sucrose and an enzyme combination from an SST and an FFT of the invention. In a further embodiment the present invention relates to an in vitro method for producing inulin by using a mixture containing fructosyl oligomers and an FFT of the invention. In this context, a fructosyl oligomer is an oligomer consisting of fructose units with a DP of approximately 2 to 7 which may exhibit a glucose residue at its end. When carrying out the method of the invention, recombinantly produced proteins are preferably used. In the context of the present invention these are proteins which were produced by introducing the respective protein-encoding DNA sequence into a host cell and expressing it there. The protein may subsequently be recovered from the host cell and/or from the culture medium. The host cell is preferably a host cell of the invention as defined above. In a preferred embodiment of the method of the invention enzymes are used which were recombinantly produced and secreted into the culture medium by the host cell, so that it is not necessary to disrupt the cells or to further purify the protein since the secreted protein may be obtained from the supernatant. In order to remove the residues of the culture medium, conventional processing techniques may be used such as dialysis, reverse osmosis, chromatographic methods etc. The same holds true for concentrating the protein secreted in the culture medium. The secretion of proteins by microorganisms is normally mediated by N-terminal signal peptides (signal sequence, leader peptide). Proteins with this signal sequence may penetrate the cell membrane of the microorganism. A secretion of proteins may be achieved by linking the DNA sequence encoding this signal peptide to the corresponding enzyme-encoding region. Use is preferably made of the signal peptide of the α-CGTase from Klebsiella oxytoca M5A1 (Fiedler et al., J. Mol. Biol. 256 (1996), 279–291) or of a signal peptide as it is encoded by the nucleotides 11529–11618 of the sequence deposited in the gene bank with the accession number X86014.

The enzymes used in the method of the invention may alternatively be produced not by using microorganisms but by means of an in vitro transcription and translation system which leads to the expression of the proteins. In a particularly preferred embodiment of the invention the FFT is produced from the protoplasts of the leave tissue in plants.

The invention further relates to inulin which may be formed from a host cell, in particular a plant cell, plant tissue or a plant of the invention or from the propagation material or the harvest product of the plants and plants cells of the invention or which is obtained by one of the above-described methods of the invention. This inuslin may preferably be used in order to produce surfactants for increasing the viscosity in aqueous system, as a suspending agent, for speeding up sedimentation, for complexing or for binding water.

These or other embodiments have been disclosed and are evident to the skilled person. They are comprised by the description and the examples of the present invention. Further literature that relates to one of the above-mentioned methods, means or uses and that can be applied in the sense of the present invention, may be taken from the prior art, e.g. from public libraries or by utilizing electronic means. Public data bases serve this purpose, as e.g. "Medline" which may be accessed via Internet. Further data bases and addresses are known to the person skilled in the art and may be taken from the Internet. A survey of sources and information regarding biotechnology patents or patent applications can be found in Berks, TIBTECH 12 (1994), 352–364.

DETAILED DESCRIPTION OF THE INVENTION

The Examples illustrate the invention.

EXAMPLE 1

Identification, Isolation and Characterization of a cDNA Encoding a Fructosyl Transferase from Artichoke (Cynara scolymus)

Total RNA was isolated from the receptacles of artichoke (Sambrook et al., 1989, Molecular Cloning, A Laboratory Manual, $2^{nd}$ edition, Cold Spring Harbor Laboratory Press, Cold Spring Harbor, N.Y., USA). Poly(A)+ mRNA was isolated by means of the mRNA isolation system PolyATract (Promega Corporation, Madison, Wis., USA). Complementary DNA (cDNA) was produced from 5 μg of this RNA by means of the ZAP-cDNA synthesis kit of Stratagene (Heidelberg) according to the manufacturer's instructions, and $2 \times 10^6$ independent recombinant phage clones were obtained. The amplified cDNA library was screened according to standard methods under low stringency conditions by means of the $^{32}$P-labeled DNA fragment corresponding to the cDNA of the SST from artichoke (Not I-fragment of the plasmid pCy21 as described in DE 197 08 774.4). The sequence of the SST from artichoke has been described in DE 197 08 774.4. Positive clones were screened by means of the SST probe under high stringency. Clones which reacted positively during this screening were abandoned since they were evidently SST cDNA. From the residual clones the cDNA insert was isolated by cleaving the plasmid DNA isolated in standard routines by means of the restriction enzyme NotI and was cloned into the vector pA7. The sticky ends of the NotI fragment were filled in by means of the T4 polymerase. Subsequently, the fragment was ligated into the SmaI site of pA7. The vector pA7 is a derivative of pUC18 (Yanish-Perron, Gene 33 (1985), 103–119) which contains an insert of the 35S promoter of the Cauliflower-Mosaic virus (nucleotide 7146 to 7464 according to Gardner, Nucleic Acids Res. 9 (1981), 2871–2888) between the EcoRI and the SacI site of the polylinker. Apart from the 35S promoter, pA7 contains the polyadenylation signal of gene 3 of the T-DNA of the Ti plasmid pTi ACH 5 (Gielen, EMBO J. 3 (1984), 835–846), nucleotides 11749 to 11939, which was isolated as a Pvu II-Hind III fragment from the plasmid pAGV 40 (Herrera-Estrella, Nature 303 (1983), 209–213) and cloned between the SphI and the Hind III site of the polylinker after adding Sph I linkers to the Pvu II site.

Figure 1:
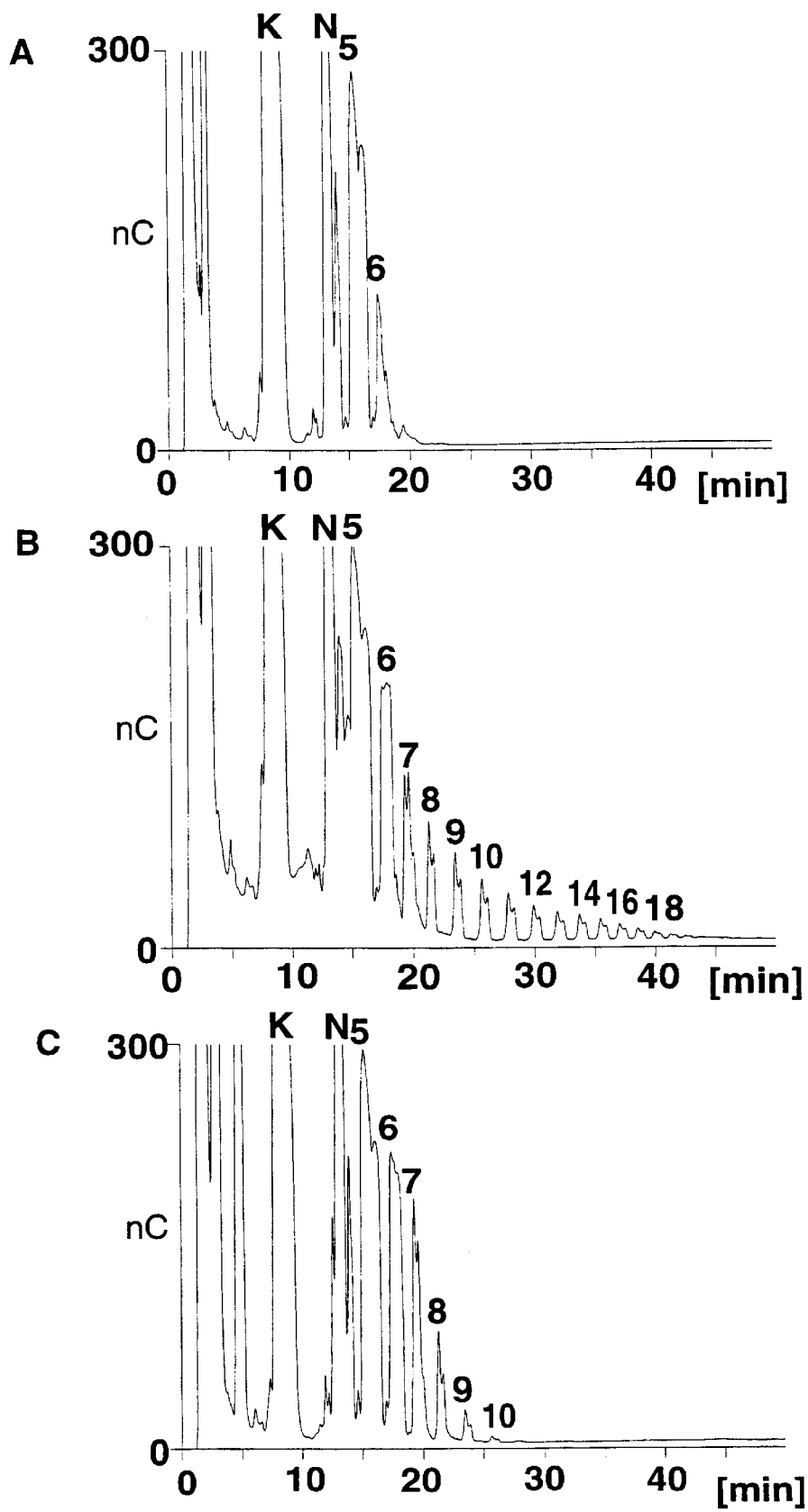
FIG. 1 shows the HPLC analysis of a complete protoplast extract. The protoplasts were transformed with various vectors: A: transformation was carried out with the vector pA7 that does not contain a coding region fused to the CaMV 35S promoter. B: transformation took place with the vector pA7-csFFT which contains the coding region of the fructan:fructan-fructosyl transferase from artichoke fused to the CaMV 35S promoter. C: transformation was carried out with the vector pA7-htFFT which contains the coding region of the fructan:fructan fructosyl transferase from Helianthus tuberosus as a fusion to the CaMV 35S promoter. Before analysis, the complete protoplast extracts were incubated in a mixture of fructosyl oligomers for 12 h each. Analysis was carried out as described in Example 1.

By means of the pA7 derivatives which contained a cDNA from artichoke, tobacco protoplasts were transformed according to the method of Negrutiu (Plant Mol. Biol. 8, (1987), 363–373). The transformed protoplasts were cultivated in K3 medium (Nagy and Maliga, Z. Pflanzenphysiologie 78 (1976), 453–455) at 25° C. for two days in the dark. Subsequently, the cell extracts were obtained by repeated freezing and thawing. The extracts were incubated with oligofructans (67.5% 1-kestose, 28.4% nystose, 3.6% fructosyl nystose, 0.5% sucrose) for 12 h at 28° C. and subsequently analyzed by HPLC. The HPLC analysis was carried out with a CarboPac PA 100 anionic exchange column, which was connected to a Dionex DX-300 gradient chromatography system (Dionex, Sunnyvale, Calif., USA). Sugar monomers, oligomers and polymers were detected by means of pulsamperometric detection. The detector adjustment for this purpose was: $T_1$=0.48s; $T_2$=0.12s; $T_3$=0.12s; $E_1$=0.05V; $E_2$=0.65V; $E_3$=−0.95V; sensibility=0.1 μC; integration =0.28–0.48s; flow medium A=0. 15 M NaOH; flow medium B=1 M NaAc in 0.15 M NaOH; gradient: 10 min 100% A; 2 min linear increase from 0% B to 100% B; 2 min 100% B; 2 min linear increase from=0% A to 100% A; 5 min A. The samples were desalinated and filtered (microcon 10, amicon, Beverly, USA) before application. The flow speed was 1 ml min$^{-1}$. In a few extracts, high-molecular inulin could be found (cf. FIG. 1).

EXAMPLE 2

Sequence Analysis of the cDNA Insert of the Plasmid pCy3

A cDNA insert from a pA7 derivative (pCy3) which had mediated the synthesis of high-molecular inulin in the protoplast assay was sequences by means of the didesoxy-nucleotide technique (Sanger, Proc. Natl. Acad. Sci. USA 74 (1977), 5463–5467). The insert of the clone pCy3 is a DNA with a length of 2073 bp. The nucleotide sequence is indicated under SEQ ID No. 1. The corresponding amino acid sequence is indicated under SEQ ID No. 2. SEQ ID No. 3 is a variant of SEQ ID No. 1 which encodes the same protein as that encoded by SEQ ID No. 1.

A sequence analysis and a comparison with already published sequences has shown that the sequence indicated under SEQ ID No. 1 is novel and comprises a coding region exhibiting homologies to FFTs from other organisms.

EXAMPLE 3

Figure 2:
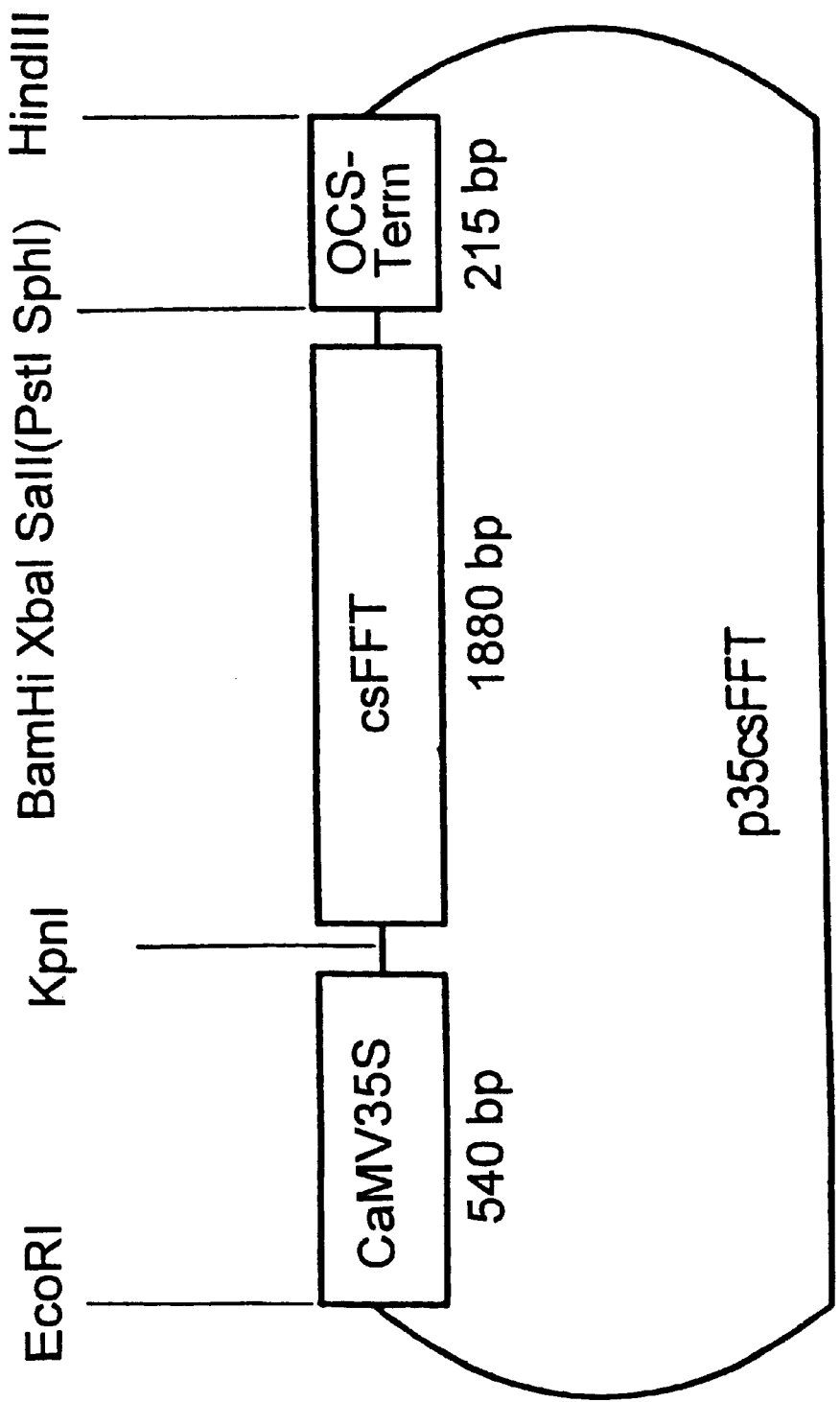
FIG. 2 shows the construction of the plasmid p35-csFFT

Synthesis of the Plasmid p35-csFFT and Integration of the Plasmid into the Potato Genome The plasmid p35-csFFT (FIG. 2) contains three fragments A, B and C within the binary vector pBin19 (Bevan, Nucl. Acids Res. 12 (1984), 8711, modified according to Becker, Nucleic Acids Res. 18 (1990), 203).

The fragment A contains the 35S promoter of the Cauliflower-Mosaic virus (CaMV). It contains the nucleotides 7146 to 7464 (Gardner, Nucleic Acids Res. 9 (1981), 2871–2888) as an insert between the EcoRI and the SacI site of the polylinker of pBin19-Hyg.

The fragment B contains the nucleotides 1 to 2073 of the sequence SEQ ID No. 1. The fragment B was obtained as a Not I fragment from the vector pBK-CMV into which it was inserted at the EcoRI site via an EcoRI/Not I linker sequence. The fragment C contains the polyadenylation signal of the gene 3 of the T-DNA of the Ti plasmid pTi ACH 5 (Gielen, EMBO J. 3 (1984), 835–846), nucleotide 11749 to 11939, which was isolated as a Pvu II-Hind III fragment from the plasmid pAGV 40 (Herrera-Estrella, Nature 303 (1983), 209–213) and cloned between the SphI and the Hind III site of the polylinker of pBin19-Hyg after adding Sph I linkers to the Pvu II site.

Figure 3:
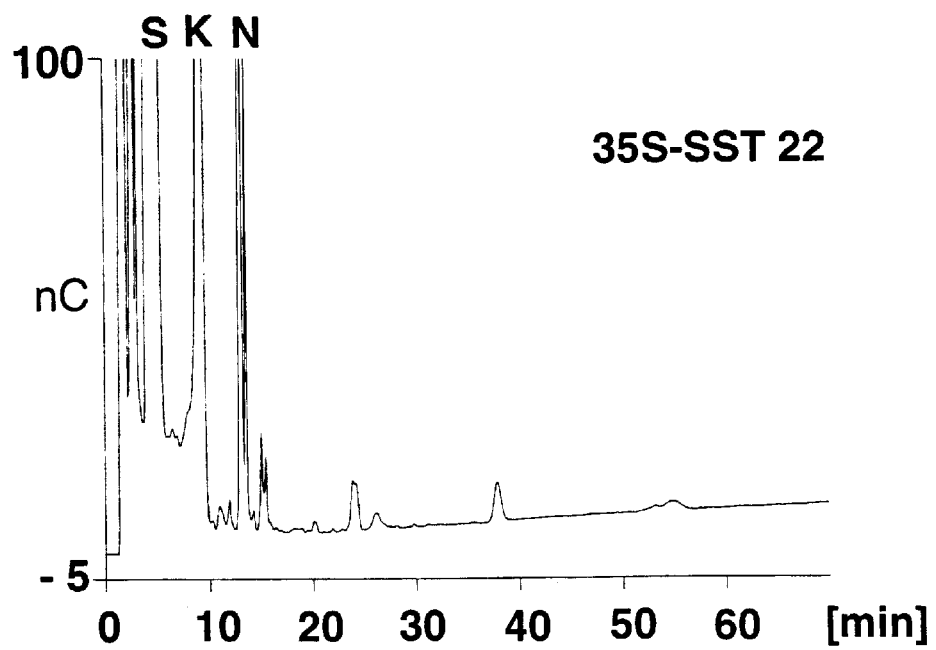
FIG. 3 shows the HPLC analysis of transgenic plants which were transformed with the construct p35-csFFT. The analysis shows that long-chain inulin molecules were formed in transgenic plants which express an SST as well as an FFT from artichoke (35S-SST/FFT 22/19).
Figure 3:
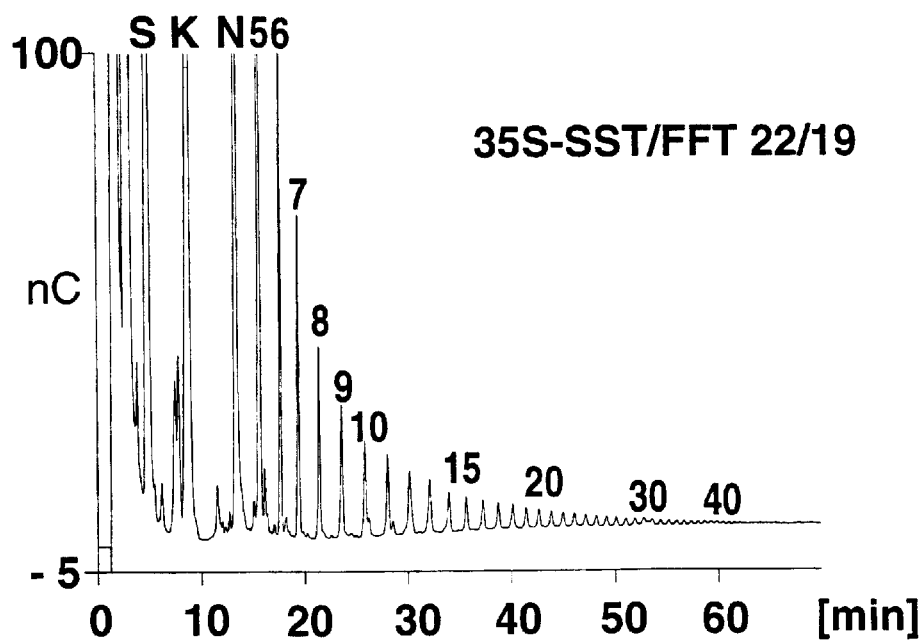

The plasmid p35-csSST was introduced into Agrobacteria (Höfgen and Willmitzer, Nucleic Acids Res. 16 (1988), 9877) and subsequently introduced into potato plants via the Agrobacterium-mediated gene transfer according to the above-described standard techniques. Said potato plants were transformed with a DNA sequence encoding an SST from artichoke (see German patent application DE-A1 197 08 774) and which express these sequences under the control of the 35S promoter. Intact plants were regenerated from transformed cells. Extracts were obtained from the leaves of regenerated plants and examined with respect to the presence of fructosyl polymers. The analysis was carried out as described in Example 1. The analysis of leaves from a range of plants transformed with this vector system unambiguously proved the occurrence of high-molecular inulin, which results from the expression of the FFT gene from artichoke contained in p35-csFFT (cf. FIG. 3).

TABLE I

Analysis of inulin content of transgenic potato tubers expressing an artichoke SST and FFT gene

| Plant No. | fructan content μmol fructose/g fresh weight | average degree of polymerization (fructose/glucose ration) |
|---|---|---|
| 35-SST/FFT 22/26 | 30.81 | 21 (20/1) |
| 35-SST/FFT 36/17 | 27.34 | 20 (19/1) |

Figure 4:
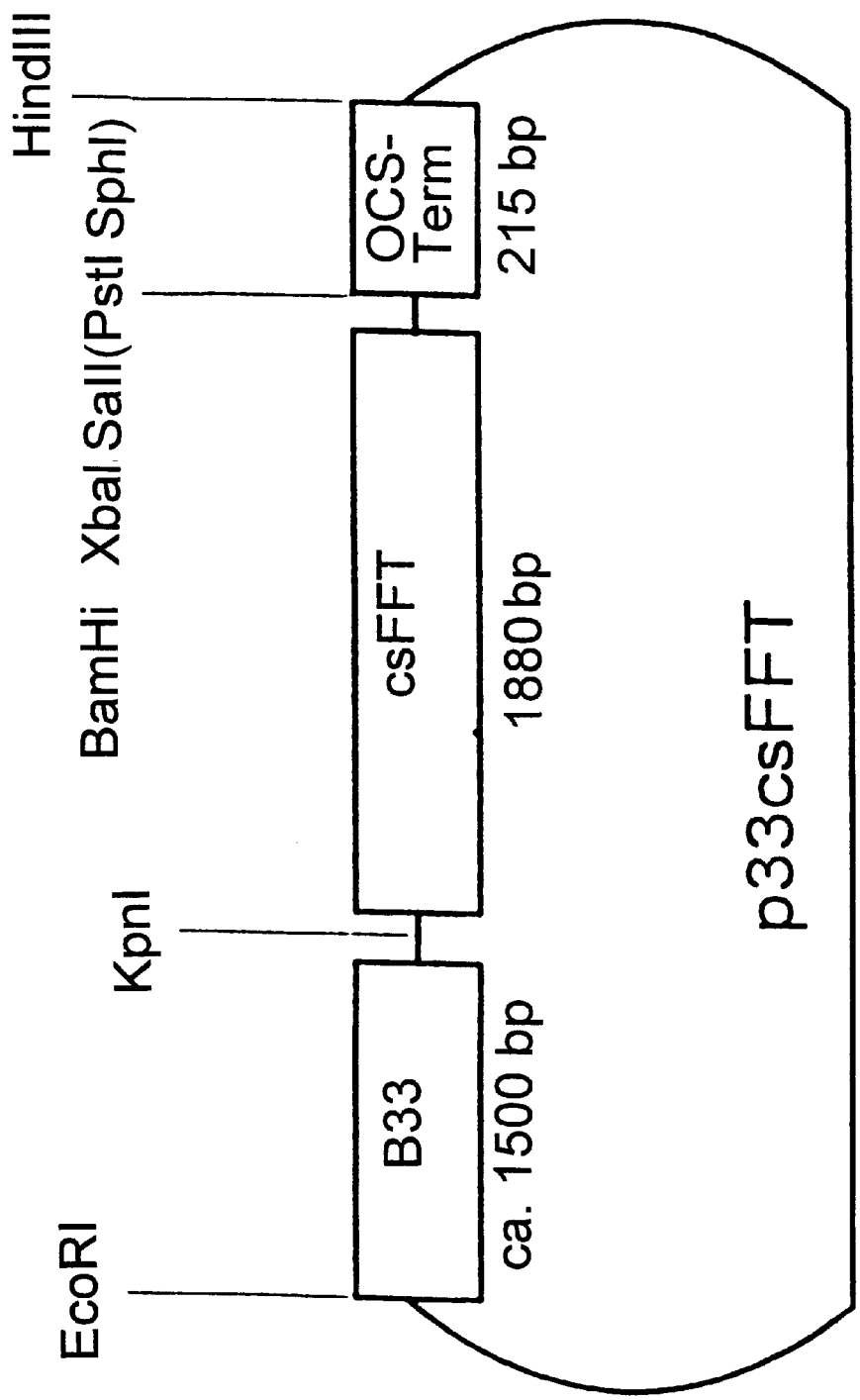
FIG. 4 shows the construction of the plasmid p33-csFFT
Figure 5:
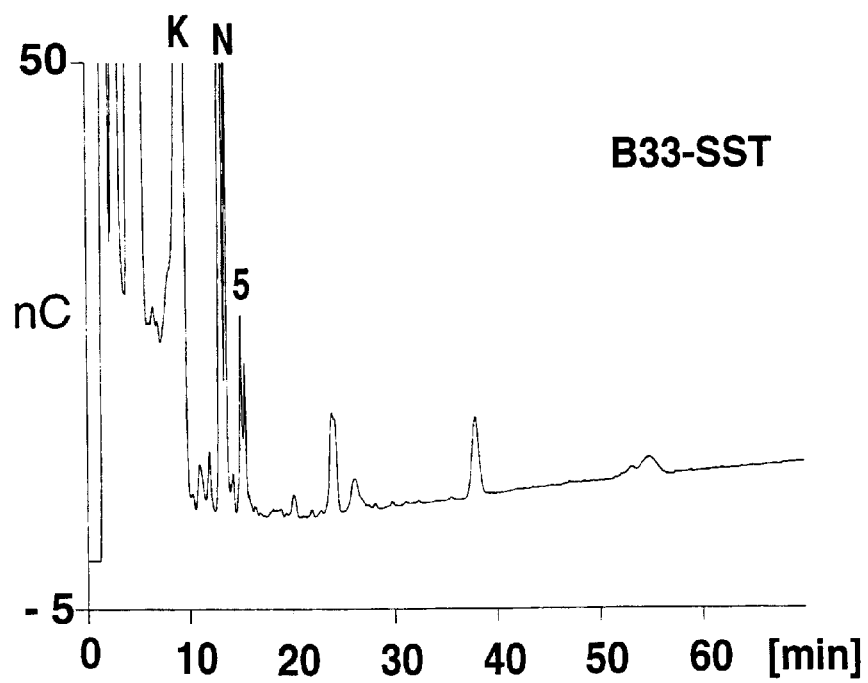
FIG. 5 shows the HPLC analysis of transgenic plants which were transformed with the construct p33-csFFT. The analysis shows that long-chain inulin molecules were formed in transgenic plants which express an SST as well as an FFT from artichoke (B33-SST/FFT 47).
Figure 5:
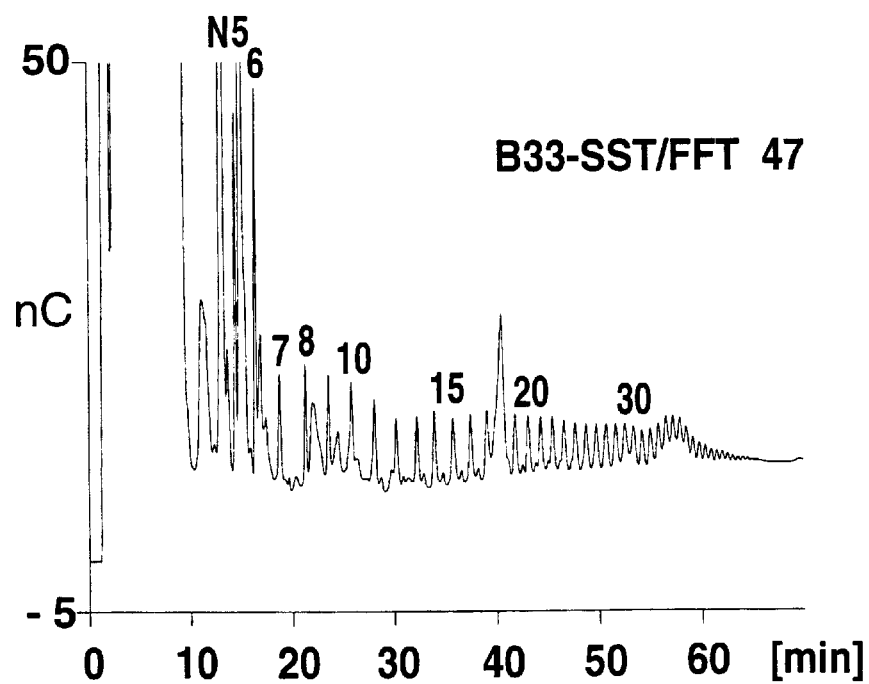

EXAMPLE 4
Production of the Plasmid p33-csFFT and Integration of the Plasmid into the Potato Genome The plasmid p33-csFFT (FIG. 4) is identical with the plasmid p35-csFFT, with the exception that the fragment A contains the B33 promoter of the patatin gene b33 from potato instead of the 35S promoter of CaMV. It contains a DraI fragment (position −1512 to position +14) of the patatin gene b33 (Rocha-Sosa, EMBO J. 8 (1989), 23–29), which was inserted between the EcoRI and the SacI site of the polylinker of pBin19-Hyg. The plasmid p33-csFFT has a size of approximately 14 kb. The plasmid p33-csSST was introduced into potato plants via the Agrobacterium-mediated gene transfer, as described in Example 3. Said potato plants were transformed with a DNA sequence encoding an SST from artichoke (see German patent application E-A1 197 08 774) and which expressed these sequences under the control of the B33 promoter. Intact plants were regenerated from transformed cells. The analysis of tubers from a range of plants transformed with this vector system unambiguously proved the occurrence of high-molecular inulin, which results from the expression of the FFT gene from artichoke contained in p33-csFFT (cf. FIG. 5).

We claim:

1. An isolated nucleic acid molecule comprising a acid sequence encoding a fructosyl transferase (FFT) protein, wherein the nucleic acid sequence is selected from the group consisting of:

(a) a nucleic acid sequence encoding a protein comprising the amino acid sequence of SEQ ID NO: 2 or SEQ ID NO: 4;

(b) a nucleic acid sequence comprising the coding region of SEQ ID NO: 1 or SEQ ID NO: 3;

(c) a nucleic acid sequence that hybridizes to a complementary strand of the nucleic acid sequence named under (a) or (b) under conditions of hybridization in 50% formamide, 5×SSC, 5×Denhardt's solution, 40 mM sodium phosphate pH 6.8; 0.5% (w/v) BSA, 1% (w/v) SDS and 0.1 mg/ml herring sperm DNA at 42° C. and washing in 0.5×SSC/0.5% SDS at 60° C.; and (d) a nucleic acid sequence comprising a fragment of the nucleotide sequence of (a), (b) or (c), said fragment being of a length sufficient to encode a FFT protein.

2. The nucleic acid molecule according to claim 1, wherein the molecule is a DNA molecule.

3. The nucleic acid molecule according to claim 2, wherein the molecule is a cDNA molecule.

4. The nucleic acid molecule according to claim 1, wherein the molecule is an RNA molecule.

5. The nucleic acid molecule according to any one of claims 1 to 4 that is derived from artichoke.

6. An isolated nucleic acid molecule comprising a nucleic acid sequence selected from the group consisting of the coding region of SEQ ID NO: 1, the coding region of SEQ ID NO: 3, a nucleic acid sequence encoding a protein comprising the amino acid sequence of SEQ ID NO: 2, and a nucleic acid sequence encoding a protein comprising the amino acid sequence of SEQ ID NO: 4.

7. An isolated nucleic acid molecule comprising a nucleic acid sequence encoding a fructosyl transferase (FFT) protein, wherein the nucleic acid sequence is more than 80% identical to a nucleic acid sequence selected from the group consisting of:

(a) a nucleic acid sequence encoding a protein comprising the amino acid sequence of SEQ ID NO: 2 or SEQ ID NO: 4;

(b) the coding region of SEQ ID NO: 1 or SEQ ID NO: 3; and (c) a nucleic acid sequence comprising a fragment of the nucleotide sequence of (a) or (b), wherein the fragment encodes a fructosyl transferase (FFT) protein.

8. An isolated nucleic acid molecule comprising a nucleic acid sequence encoding a fructosyl transferase (FFT) protein, wherein the nucleic acid sequence is more than 90% identical to a nucleic acid sequence selected from the group consisting of:

(a) a nucleic acid sequence encoding a protein comprising the amino acid sequence of SEQ ID NO: 2 or SEQ ID NO: 4;

(b) the coding region of SEQ ID NO: 1 or SEQ ID NO: 3; and (c) a nucleic acid sequence comprising a fragment of the nucleotide sequence of (a) or (b), wherein the fragment encodes a fructosyl transferase (FFT) protein.

9. A vector comprising the nucleic acid molecule according to any one of claims 1–4 or 6–8.

10. The vector according to claim 9, wherein the nucleic acid molecule is operatively linked to a regulatory element ensuring the transcription and synthesis of a translatable RNA in a prokaryotic cell a eukaryotic cell, or a procaryotic and eukaryotic cell.

11. The vector according to claim 10, wherein the regulatory element is derived from the patatin B33 promoter or the CaMV 35S promoter.

12. A host cell transformed with the nucleic acid molecule according to any one of claims 1–4 or 6–8, or a host cell that comprises a vector comprising the nucleic acid molecule, or a derivative of said host cell, wherein said derivative comprises said nucleic acid molecule.

13. The host cell according to claim 12, wherein the cell additionally comprises a nucleic acid molecule comprising a nucleic acid sequence encoding a sucrose-dependent sucrose fructosyl transferase (SST).

14. A method for the production of an FFT, comprising the steps of cultivating the host cell according to claim 12 under conditions allowing for the synthesis of the FFT.

15. An isolated nucleic acid molecule that specifically hybridizes to the nucleic acid molecule according to claim 6 or to a complementary strand thereof under conditions of hybridization in 50% formamide, 5×SSC. 5×Denhardt's solution 40 mM sodium phosphate pH 6.8; 0.5% (w/v) BSA, 1% (w/v) SDS and 0.1 mg/ml herring sperm DNA at 42 degrees C and washing in 0.5×SSC/0.5% SDS at 60 degrees C.

16. A method for the production of a host cell, a transgenic plant cell, a transgenic plant tissue or a transgenic plant, comprising the step of introducing the nucleic acid molecule according to any one of claims 1–4 or 6–8, or a vector comprising said nucleic acid molecule, into the host cell, the plant cell, the plant tissue or the plant.

17. A transgenic plant cell or plant tissue that comprises the nucleic acid molecule according to any one of claims 1–4 or 6–8, or that comprises a vector comprising said nucleic acid molecule, or a derivative of said cell or tissue, wherein said derivative comprises said nucleic acid molecule.

18. The transgenic plant cell, plant tissue or plant according to claim 17, additionally comprising a nucleic acid molecule comprising a nucleic acid sequence that encodes a sucrose-dependent sucrose fructosyl transferase.

19. A plant comprising the plant cell or plant tissue according to claim 17, or comprising said plant cell or said plant tissue that additionally comprises a gene encoding an SST.

20. The plant according to claim 19, wherein the plant is a sucrose-containing plant.

21. The plant according to claim 20, wherein the sucrose-containing plant is selected from the group consisting of a rice, maize, sugar beet, sugar cane, potato, tomato, carrot, leek, chicory, sweet potato, wheat, barley, rape and soybean plant.

22. A propagation material of a plant comprising the plant cell according to claim 15 or comprising said plant cell that additionally comprises a gene encoding an SST.

23. A harvest product of a plant comprising a plant cell according to claim 17 or comprising said plant cell that additionally comprises a gene encoding an SST.

24. A method for the production of high molecular inulin comprising (a) cultivating the host cell according to claim 12; or a transgenic plant cell, plant tissue or plant comprising said host cell; or said host cell, transgenic plant cell, plant tissue or plant that additionally comprise a gene encoding SST, under conditions which allow for the production of an FFT and the conversion of 1-kestose or an equivalent substrate into high molecular inulin, wherein 1-kestose or the equivalent substrate is optionally added to the culture, and (b) recovering the thus produced inulin from the cultivated cell, tissue or plant or from a medium in which the cell or tissue may have been cultivated.

25. The isolated nucleic acid molecule according to claim 6, wherein the nucleic acid sequence is SEQ ID NO: 1 or SEQ ID NO: 3.

26. The vector according to claim 9, wherein the nucleic acid molecule is derived from artichoke.

27. The host cell according to claim 12, wherein the nucleic acid molecule is derived from artichoke.

28. The method according to claim 16, wherein the nucleic acid molecule is derived from artichoke.

29. The transgenic plant cell or plant tissue according to claim 17, wherein the nucleic acid molecule is derived from artichoke.

* * * * *

UNITED STATES PATENT AND TRADEMARK OFFICE
CERTIFICATE OF CORRECTION

PATENT NO. : 6,559,356 B1
DATED : May 6, 2003
INVENTOR(S) : Arnd G. Heyer et al.

It is certified that error appears in the above-identified patent and that said Letters Patent is hereby corrected as shown below:

Title page,
Item [57], ABSTRACT,
Line 3, replace "inulin Nucleic" with -- inulin. Nucleic --.

Column 2,
Line 41, replace "PCT/NL9300279" with -- PCT/NL93/00279 --.
Line 44, replace "inuin" with -- inulin --.
Line 49, replace "Chafterton" with -- Chatterton --.

Column 4,
Line 9, replace "synthesis," with -- synthesis --.
Line 63, replace "60° C." with -- 60° C --.

Column 10,
Line 9, replace "Jahne" with -- Jaehne --.

Column 11,
Line 5, replace "a" with -- as --.

Column 12,
Line 20, replace "inuslin" with -- inulin --.
Line 22, replace "system," with -- systems as detergent, --.

Column 13,
Line 16, replace "Wis." with -- WI --.
Line 54, replace "25° C." with -- 25° C --.
Line 58, replace "28° C." with -- 28° C --.

Column 31,
Line 6, replace "42° C." with -- 42° C --.
Line 7, replace "60° C." with -- 60° C --.
Lines 58-59, replace "prokaryotic cell a eukaryotic cell, or a procaryotic and eukaryotic cell." with -- prokaryotic cell, a eukaryotic cell or a prokaryotic and eukaryotic cell --.

UNITED STATES PATENT AND TRADEMARK OFFICE
CERTIFICATE OF CORRECTION

PATENT NO. : 6,559,356 B1
DATED : May 6, 2003
INVENTOR(S) : Arnd G. Heyer et al.

It is certified that error appears in the above-identified patent and that said Letters Patent is hereby corrected as shown below:

Column 32,
Line 11, replace "5xSSC." with -- 5xSSC, --.
Lines 14-15, replace "42 degrees C" with -- 42° C --.
Lines 15-16, replace "60 degrees C." with -- 60° C. --.
Line 47, replace "claim 15" with -- claim 17 --.

Signed and Sealed this

Twenty-first Day of June, 2005

JON W. DUDAS
*Director of the United States Patent and Trademark Office*

SEQUENCE LISTING

<160> NUMBER OF SEQ ID NOS:  4

<210> SEQ ID NO 1
<211> LENGTH: 2073
<212> TYPE: DNA
<213> ORGANISM: Cynara scolymus
<220> FEATURE:
<221> NAME/KEY: CDS
<222> LOCATION: (21)..(1871)

<400> SEQUENCE: 1

```
ttacctcatt tccatcaacc atg aga acg act gaa ccc caa act gac ctt gag      53
                     Met Arg Thr Thr Glu Pro Gln Thr Asp Leu Glu
                      1               5                  10 cat gca ccc aac cac act cca cta ctg gac cac ccc gaa cca cca ccg       101
His Ala Pro Asn His Thr Pro Leu Leu Asp His Pro Glu Pro Pro Pro
             15                  20                  25 gcc gcc gtg aga aac cgg ttg ttg att agg gtt tcg tcc agt atc aca       149
Ala Ala Val Arg Asn Arg Leu Leu Ile Arg Val Ser Ser Ser Ile Thr
         30                  35                  40 ttg gtc tct ctg ttt ttt gtt tca gca ttc cta ctc att ctc ctg tac       197
Leu Val Ser Leu Phe Phe Val Ser Ala Phe Leu Leu Ile Leu Leu Tyr
     45                  50                  55 caa cac gat tcc act tac acc gat gat aat tca gca ccg tcg gaa agt       245
Gln His Asp Ser Thr Tyr Thr Asp Asp Asn Ser Ala Pro Ser Glu Ser
 60                  65                  70                  75 tct tcc cag cag ccc tcc gct gcc gat cgc ctg aga tgg gag aga aca       293
Ser Ser Gln Gln Pro Ser Ala Ala Asp Arg Leu Arg Trp Glu Arg Thr
                 80                  85                  90 gct ttt cat ttc cag ccc gcc aaa aat ttc att tat gat ccc aac ggt       341
Ala Phe His Phe Gln Pro Ala Lys Asn Phe Ile Tyr Asp Pro Asn Gly
             95                 100                 105 cca ttg ttc cat atg ggt tgg tac cat ctt ttc tac caa tac aac ccg       389
Pro Leu Phe His Met Gly Trp Tyr His Leu Phe Tyr Gln Tyr Asn Pro
        110                 115                 120 tac gca ccg ttt tgg ggc aac atg aca tgg ggt cac gcc gtg tcc aaa       437
Tyr Ala Pro Phe Trp Gly Asn Met Thr Trp Gly His Ala Val Ser Lys
    125                 130                 135 gac atg atc aac tgg ttc gag ctt ccg atc gcc ttg gcc cca acc gaa       485
Asp Met Ile Asn Trp Phe Glu Leu Pro Ile Ala Leu Ala Pro Thr Glu
140                 145                 150                 155 tgg tac gat atc gag ggt gtt tta tca ggc tca acc acg atc ctc cct       533
Trp Tyr Asp Ile Glu Gly Val Leu Ser Gly Ser Thr Thr Ile Leu Pro
                160                 165                 170
```

-continued

```
gat ggt cga atc ttt gct ctc tat acc gga aac aca aac gat ctc gag      581
Asp Gly Arg Ile Phe Ala Leu Tyr Thr Gly Asn Thr Asn Asp Leu Glu
            175                 180                 185 caa ctt caa tgc aaa gcc gtg cca gtt aat gca tcc gac cca ctt ctt      629
Gln Leu Gln Cys Lys Ala Val Pro Val Asn Ala Ser Asp Pro Leu Leu
        190                 195                 200 gtt gaa tgg gtc agg tac gat gct aac ccg atc ctg tat gct cca tca      677
Val Glu Trp Val Arg Tyr Asp Ala Asn Pro Ile Leu Tyr Ala Pro Ser
    205                 210                 215 ggg atc ggg tta aca gat tac cgg gac ccg tca aca gtt tgg acg ggt      725
Gly Ile Gly Leu Thr Asp Tyr Arg Asp Pro Ser Thr Val Trp Thr Gly
220                 225                 230                 235 ccc gat gga aaa cat cgg atg atc ata ggg act aaa cga aat act aca      773
Pro Asp Gly Lys His Arg Met Ile Ile Gly Thr Lys Arg Asn Thr Thr
                240                 245                 250 gga ctc gta ctt gta tac cat acc acc gat ttc aca aac tac gta atg      821
Gly Leu Val Leu Val Tyr His Thr Thr Asp Phe Thr Asn Tyr Val Met
            255                 260                 265 ttg gac gag ccg ttg cac tcg gtc ccc aac act gat atg tgg gaa tgt      869
Leu Asp Glu Pro Leu His Ser Val Pro Asn Thr Asp Met Trp Glu Cys
        270                 275                 280 gtc gac ctt tac cct gtg tca acg acc aac gat agt gca ctt gat gtt      917
Val Asp Leu Tyr Pro Val Ser Thr Thr Asn Asp Ser Ala Leu Asp Val
    285                 290                 295 gcg gcc tat ggt ccg ggt atc aag cat gtg ctt aaa gaa agt tgg gag      965
Ala Ala Tyr Gly Pro Gly Ile Lys His Val Leu Lys Glu Ser Trp Glu
300                 305                 310                 315 gga cac gcg atg gac ttt tac tcg atc ggg aca tac gat gca ttt aac     1013
Gly His Ala Met Asp Phe Tyr Ser Ile Gly Thr Tyr Asp Ala Phe Asn
                320                 325                 330 gat aag tgg aca ccc gat aat ccc gaa cta gac gtc ggt atc ggg ttg     1061
Asp Lys Trp Thr Pro Asp Asn Pro Glu Leu Asp Val Gly Ile Gly Leu
            335                 340                 345 cgg tgc gat tac gga agg ttc ttt gcg tcg aag agc ctc tac gac ccg     1109
Arg Cys Asp Tyr Gly Arg Phe Phe Ala Ser Lys Ser Leu Tyr Asp Pro
        350                 355                 360 ttg aag aaa cga aga gtc act tgg ggt tat gtt gcg gaa tcc gac agt     1157
Leu Lys Lys Arg Arg Val Thr Trp Gly Tyr Val Ala Glu Ser Asp Ser
    365                 370                 375 tac gac caa gac gtc tct aga gga tgg gct act att tat aat gtt gca     1205
Tyr Asp Gln Asp Val Ser Arg Gly Trp Ala Thr Ile Tyr Asn Val Ala
380                 385                 390                 395 agg acc att gta ctc gat cgg aag act gga acc cat cta ctt caa tgg     1253
Arg Thr Ile Val Leu Asp Arg Lys Thr Gly Thr His Leu Leu Gln Trp
                400                 405                 410 ccg gtg gag gaa atc gag agc ttg aga tcc aac ggt cat gaa ttc aaa     1301
Pro Val Glu Glu Ile Glu Ser Leu Arg Ser Asn Gly His Glu Phe Lys
            415                 420                 425 aat ata aca ctt gag ccg ggc tcg atc att ccc ctc gac gta ggc tca     1349
Asn Ile Thr Leu Glu Pro Gly Ser Ile Ile Pro Leu Asp Val Gly Ser
        430                 435                 440 gct acg cag ttg gac atc gtt gca aca ttt gag gtg gat caa gag gcg     1397
Ala Thr Gln Leu Asp Ile Val Ala Thr Phe Glu Val Asp Gln Glu Ala
    445                 450                 455 tta aaa gca aca agt gac acg aac gac gaa tac ggt tgc acc aca agt     1445
Leu Lys Ala Thr Ser Asp Thr Asn Asp Glu Tyr Gly Cys Thr Thr Ser
460                 465                 470                 475 tcg ggt gca gcc aaa ggg gaa gtt ttg gac cat tcg ggg att gca gtt     1493
Ser Gly Ala Ala Lys Gly Glu Val Leu Asp His Ser Gly Ile Ala Val
```

-continued

```
                      480                 485                 490
ctt gcc cac gga acc ctt tcg gag tta act ccg gtg tat ttc tac att        1541
Leu Ala His Gly Thr Leu Ser Glu Leu Thr Pro Val Tyr Phe Tyr Ile
            495                 500                 505 gct aaa aac acc aag gga ggt gtg gat aca cat ttt tgt acg gat aaa        1589
Ala Lys Asn Thr Lys Gly Gly Val Asp Thr His Phe Cys Thr Asp Lys
        510                 515                 520 cta agg tca tca tat gat tat gat ggt gag aag gtg gtg tat ggc agc        1637
Leu Arg Ser Ser Tyr Asp Tyr Asp Gly Glu Lys Val Val Tyr Gly Ser
    525                 530                 535 acc gtc cca gtg ctc gac ggc gaa gaa ttc aca atg agg ata ttg gtg        1685
Thr Val Pro Val Leu Asp Gly Glu Glu Phe Thr Met Arg Ile Leu Val
540                 545                 550                 555 gat cat tcg gtg gtg gag ggg ttt gca caa ggg gga agg aca gta ata        1733
Asp His Ser Val Val Glu Gly Phe Ala Gln Gly Gly Arg Thr Val Ile
                560                 565                 570 acg tca aga gtg tat ccc acg aaa gca ata tac gaa gca gcc aag ctt        1781
Thr Ser Arg Val Tyr Pro Thr Lys Ala Ile Tyr Glu Ala Ala Lys Leu
            575                 580                 585 ttc gtc ttc aac aat gcc act acg acc agt gtg aag gcg act ctc aag        1829
Phe Val Phe Asn Asn Ala Thr Thr Thr Ser Val Lys Ala Thr Leu Lys
        590                 595                 600 gtc tgg caa atg tct caa gcc ttt gtc aag gct tat ccg ttt                1871
Val Trp Gln Met Ser Gln Ala Phe Val Lys Ala Tyr Pro Phe
    605                 610                 615 tagttttta tgcatctttt taagacattg ttgtttcata tgattcaagt tttatctgtg       1931
tgttatgtta agacacgcag cttaaaatag ccacatgtga gatcatttgc gtatggccgt      1991
caactatttt ttaatatgca acttcagtaa tgctatttac agtatgtttt aaggaaaaaa      2051
aaaaaaaaaa aaaaaaaaaa aa                                               2073

<210> SEQ ID NO 2
<211> LENGTH: 617
<212> TYPE: PRT
<213> ORGANISM: Cynara scolymus

<400> SEQUENCE: 2

Met Arg Thr Thr Glu Pro Gln Thr Asp Leu Glu His Ala Pro Asn His
  1               5                  10                  15

Thr Pro Leu Leu Asp His Pro Glu Pro Pro Ala Ala Val Arg Asn
                 20                  25                  30

Arg Leu Leu Ile Arg Val Ser Ser Ile Thr Leu Val Ser Leu Phe
             35                  40                  45

Phe Val Ser Ala Phe Leu Leu Ile Leu Leu Tyr Gln His Asp Ser Thr
 50                  55                  60

Tyr Thr Asp Asp Asn Ser Ala Pro Ser Glu Ser Ser Gln Gln Pro
 65                  70                  75                  80

Ser Ala Ala Asp Arg Leu Arg Trp Glu Arg Thr Ala Phe His Phe Gln
                 85                  90                  95

Pro Ala Lys Asn Phe Ile Tyr Asp Pro Asn Gly Pro Leu Phe His Met
                100                 105                 110

Gly Trp Tyr His Leu Phe Tyr Gln Tyr Asn Pro Tyr Ala Pro Phe Trp
            115                 120                 125

Gly Asn Met Thr Trp Gly His Ala Val Ser Lys Asp Met Ile Asn Trp
        130                 135                 140

Phe Glu Leu Pro Ile Ala Leu Ala Pro Thr Glu Trp Tyr Asp Ile Glu
145                 150                 155                 160
```

```
Gly Val Leu Ser Gly Ser Thr Thr Ile Leu Pro Asp Gly Arg Ile Phe
            165                 170                 175

Ala Leu Tyr Thr Gly Asn Thr Asn Asp Leu Glu Gln Leu Gln Cys Lys
            180                 185                 190

Ala Val Pro Val Asn Ala Ser Asp Pro Leu Leu Val Glu Trp Val Arg
            195                 200                 205

Tyr Asp Ala Asn Pro Ile Leu Tyr Ala Pro Ser Gly Ile Gly Leu Thr
            210                 215                 220

Asp Tyr Arg Asp Pro Ser Thr Val Trp Thr Gly Pro Asp Gly Lys His
225                 230                 235                 240

Arg Met Ile Ile Gly Thr Lys Arg Asn Thr Thr Gly Leu Val Leu Val
            245                 250                 255

Tyr His Thr Thr Asp Phe Thr Asn Tyr Val Met Leu Asp Glu Pro Leu
            260                 265                 270

His Ser Val Pro Asn Thr Asp Met Trp Glu Cys Val Asp Leu Tyr Pro
            275                 280                 285

Val Ser Thr Thr Asn Asp Ser Ala Leu Asp Val Ala Ala Tyr Gly Pro
            290                 295                 300

Gly Ile Lys His Val Leu Lys Glu Ser Trp Glu Gly His Ala Met Asp
305                 310                 315                 320

Phe Tyr Ser Ile Gly Thr Tyr Asp Ala Phe Asn Asp Lys Trp Thr Pro
            325                 330                 335

Asp Asn Pro Glu Leu Asp Val Gly Ile Gly Leu Arg Cys Asp Tyr Gly
            340                 345                 350

Arg Phe Phe Ala Ser Lys Ser Leu Tyr Asp Pro Leu Lys Lys Arg Arg
            355                 360                 365

Val Thr Trp Gly Tyr Val Ala Glu Ser Asp Ser Tyr Asp Gln Asp Val
            370                 375                 380

Ser Arg Gly Trp Ala Thr Ile Tyr Asn Val Ala Arg Thr Ile Val Leu
385                 390                 395                 400

Asp Arg Lys Thr Gly Thr His Leu Leu Gln Trp Pro Val Glu Glu Ile
            405                 410                 415

Glu Ser Leu Arg Ser Asn Gly His Glu Phe Lys Asn Ile Thr Leu Glu
            420                 425                 430

Pro Gly Ser Ile Ile Pro Leu Asp Val Gly Ser Ala Thr Gln Leu Asp
            435                 440                 445

Ile Val Ala Thr Phe Glu Val Asp Gln Glu Ala Leu Lys Ala Thr Ser
            450                 455                 460

Asp Thr Asn Asp Glu Tyr Gly Cys Thr Thr Ser Ser Gly Ala Ala Lys
465                 470                 475                 480

Gly Glu Val Leu Asp His Ser Gly Ile Ala Val Leu Ala His Gly Thr
            485                 490                 495

Leu Ser Glu Leu Thr Pro Val Tyr Phe Tyr Ile Ala Lys Asn Thr Lys
            500                 505                 510

Gly Gly Val Asp Thr His Phe Cys Thr Asp Lys Leu Arg Ser Ser Tyr
            515                 520                 525

Asp Tyr Asp Gly Glu Lys Val Val Tyr Gly Ser Thr Val Pro Val Leu
            530                 535                 540

Asp Gly Glu Glu Phe Thr Met Arg Ile Leu Val Asp His Ser Val Val
545                 550                 555                 560

Glu Gly Phe Ala Gln Gly Gly Arg Thr Val Ile Thr Ser Arg Val Tyr
            565                 570                 575
```

```
Pro Thr Lys Ala Ile Tyr Glu Ala Ala Lys Leu Phe Val Phe Asn Asn
        580                 585                 590

Ala Thr Thr Thr Ser Val Lys Ala Thr Leu Lys Val Trp Gln Met Ser
        595                 600                 605

Gln Ala Phe Val Lys Ala Tyr Pro Phe
    610                 615

<210> SEQ ID NO 3
<211> LENGTH: 2073
<212> TYPE: DNA
<213> ORGANISM: Cynara scolymus
<220> FEATURE:
<221> NAME/KEY: CDS
<222> LOCATION: (21)..(1871)

<400> SEQUENCE: 3
```

| | | | | |
|---|---|---|---|---|
| ttacctcatt tccatcaacc atg aga acg act gaa ccc caa act gac ctt gag | | | | 53 |
|                                   Met Arg Thr Thr Glu Pro Gln Thr Asp Leu Glu | | | | |
|                                  1          5           10 | | | | |

```
cat gca ccc aac cac act cca cta ctg gac cac ccc gaa cca cca ccg      101
His Ala Pro Asn His Thr Pro Leu Leu Asp His Pro Glu Pro Pro Pro
        15                  20                  25 gcc gcc gtg aga aac cgg ttg ttg att agg gtt tcg tcc agt atc aca      149
Ala Ala Val Arg Asn Arg Leu Leu Ile Arg Val Ser Ser Ser Ile Thr
        30                  35                  40 ttg gtc tct ctg ttt ttt gtt tca gca ttc cta ctc att ctc ctg tac      197
Leu Val Ser Leu Phe Phe Val Ser Ala Phe Leu Leu Ile Leu Leu Tyr
 45                  50                  55 caa cac gat tcc act tac acc gat gat aat tca gca ccg tcg gaa agt      245
Gln His Asp Ser Thr Tyr Thr Asp Asp Asn Ser Ala Pro Ser Glu Ser
 60                  65                  70                  75 tct tcc cag cag ccc tcc gct gcc gat cgc ctg aga tgg gag aga aca      293
Ser Ser Gln Gln Pro Ser Ala Ala Asp Arg Leu Arg Trp Glu Arg Thr
                 80                  85                  90 gct ttt cat ttc cag ccc gcc aaa aat ttc att tat gat ccc aac ggt      341
Ala Phe His Phe Gln Pro Ala Lys Asn Phe Ile Tyr Asp Pro Asn Gly
                 95                 100                 105 cca ttg ttc cat atg ggt tgg tac cat ctt ttc tac caa tac aac ccg      389
Pro Leu Phe His Met Gly Trp Tyr His Leu Phe Tyr Gln Tyr Asn Pro
            110                 115                 120 tac gct ccc ttt tgg gga aac atg act tgg gga cat gcc gtc agt aag      437
Tyr Ala Pro Phe Trp Gly Asn Met Thr Trp Gly His Ala Val Ser Lys
 125                 130                 135 gat atg ata aat tgg ttt gaa tta ccg ata gcc tta gcg cca act gag      485
Asp Met Ile Asn Trp Phe Glu Leu Pro Ile Ala Leu Ala Pro Thr Glu
140                 145                 150                 155 tgg tac gac ata gaa ggt gtt ctg agt ggc agt act acc att tta cct      533
Trp Tyr Asp Ile Glu Gly Val Leu Ser Gly Ser Thr Thr Ile Leu Pro
                160                 165                 170 gac gga aga att ttc gct ctc tac acc gga aat aca aac gac ctc gag      581
Asp Gly Arg Ile Phe Ala Leu Tyr Thr Gly Asn Thr Asn Asp Leu Glu
            175                 180                 185 cag ctc cag tgt aag gcc gtg cca gtt aat gct agt gat cca tta ttg      629
Gln Leu Gln Cys Lys Ala Val Pro Val Asn Ala Ser Asp Pro Leu Leu
        190                 195                 200 gta gaa tgg gtt cgc tac gat gcc aat ccg ata tta tat gcc cct agt      677
Val Glu Trp Val Arg Tyr Asp Ala Asn Pro Ile Leu Tyr Ala Pro Ser
 205                 210                 215 ggc atc ggc ctc aca gat tac aga gat cct agt act gtg tgg acg ggc      725
Gly Ile Gly Leu Thr Asp Tyr Arg Asp Pro Ser Thr Val Trp Thr Gly
220                 225                 230                 235
```

```
cct gac ggt aaa cac cgt atg ata atc ggg acg aag agg aat acg act      773
Pro Asp Gly Lys His Arg Met Ile Ile Gly Thr Lys Arg Asn Thr Thr
                240                 245                 250 gga ctc gtc tta gta tat cac act acc gac ttt aca aat tat gta atg      821
Gly Leu Val Leu Val Tyr His Thr Thr Asp Phe Thr Asn Tyr Val Met
            255                 260                 265 ttg gac gag ccg ttg cac tcg gtc ccc aac act gat atg tgg gaa tgt      869
Leu Asp Glu Pro Leu His Ser Val Pro Asn Thr Asp Met Trp Glu Cys
        270                 275                 280 gtc gac ctt tac cct gtg tca acg acc aac gat agt gca ctt gat gtt      917
Val Asp Leu Tyr Pro Val Ser Thr Thr Asn Asp Ser Ala Leu Asp Val
285                 290                 295 gcg gcc tat ggt ccg ggt atc aag cat gtg ctt aaa gaa agt tgg gag      965
Ala Ala Tyr Gly Pro Gly Ile Lys His Val Leu Lys Glu Ser Trp Glu
300                 305                 310                 315 gga cac gcg atg gac ttt tac tcg atc ggg aca tac gat gca ttt aac     1013
Gly His Ala Met Asp Phe Tyr Ser Ile Gly Thr Tyr Asp Ala Phe Asn
                320                 325                 330 gat aag tgg aca ccc gat aat ccc gaa cta gac gtc ggt atc ggg ttg     1061
Asp Lys Trp Thr Pro Asp Asn Pro Glu Leu Asp Val Gly Ile Gly Leu
            335                 340                 345 cgg tgc gat tac gga agg ttc ttt gcg tcg aag agc ctc tac gac ccg     1109
Arg Cys Asp Tyr Gly Arg Phe Phe Ala Ser Lys Ser Leu Tyr Asp Pro
        350                 355                 360 ttg aag aaa cga aga gtc act tgg ggt tat gtt gcg gaa tcc gac agt     1157
Leu Lys Lys Arg Arg Val Thr Trp Gly Tyr Val Ala Glu Ser Asp Ser
    365                 370                 375 tac gac caa gac gtc tct aga gga tgg gct act att tat aat gtt gca     1205
Tyr Asp Gln Asp Val Ser Arg Gly Trp Ala Thr Ile Tyr Asn Val Ala
380                 385                 390                 395 agg acc att gta ctc gat cgg aag act gga acc cat cta ctt caa tgg     1253
Arg Thr Ile Val Leu Asp Arg Lys Thr Gly Thr His Leu Leu Gln Trp
                400                 405                 410 ccg gtg gag gaa atc gag agc ttg aga tcc aac ggt cat gaa ttc aaa     1301
Pro Val Glu Glu Ile Glu Ser Leu Arg Ser Asn Gly His Glu Phe Lys
            415                 420                 425 aat ata aca ctt gag ccg ggc tcg atc att ccc ctc gac gta ggc tca     1349
Asn Ile Thr Leu Glu Pro Gly Ser Ile Ile Pro Leu Asp Val Gly Ser
        430                 435                 440 gct acg cag ttg gac atc gtt gca aca ttt gag gtg gat caa gag gcg     1397
Ala Thr Gln Leu Asp Ile Val Ala Thr Phe Glu Val Asp Gln Glu Ala
    445                 450                 455 tta aaa gca aca agt gac acg aac gac gaa tac ggt tgc acc aca agt     1445
Leu Lys Ala Thr Ser Asp Thr Asn Asp Glu Tyr Gly Cys Thr Thr Ser
460                 465                 470                 475 tcg ggt gca gcc aaa ggg gaa gtt ttg gac cat tcg ggg att gca gtt     1493
Ser Gly Ala Ala Lys Gly Glu Val Leu Asp His Ser Gly Ile Ala Val
                480                 485                 490 ctt gcc cac gga acc ctt tcg gag tta act ccg gtg tat ttc tac att     1541
Leu Ala His Gly Thr Leu Ser Glu Leu Thr Pro Val Tyr Phe Tyr Ile
            495                 500                 505 gct aaa aac acc aag gga ggt gtg gat aca cat ttt tgt acg gat aaa     1589
Ala Lys Asn Thr Lys Gly Gly Val Asp Thr His Phe Cys Thr Asp Lys
        510                 515                 520 cta agg tca tca tat gat tat gat ggt gag aag gtg gtg tat ggc agc     1637
Leu Arg Ser Ser Tyr Asp Tyr Asp Gly Glu Lys Val Val Tyr Gly Ser
    525                 530                 535 acc gtc cca gtg ctc gac ggc gaa gaa ttc aca atg agg ata ttg gtg     1685
Thr Val Pro Val Leu Asp Gly Glu Glu Phe Thr Met Arg Ile Leu Val
```

```
540                 545                 550                 555
gat cat tcg gtg gtg gag ggg ttt gca caa ggg gga agg aca gta ata      1733
Asp His Ser Val Val Glu Gly Phe Ala Gln Gly Gly Arg Thr Val Ile
            560                 565                 570 acg tca aga gtg tat ccc acg aaa gca ata tac gaa gca gcc aag ctt      1781
Thr Ser Arg Val Tyr Pro Thr Lys Ala Ile Tyr Glu Ala Ala Lys Leu
        575                 580                 585 ttc gtc ttc aac aat gcc act acg acc agt gtg aag gcg act ctc aag      1829
Phe Val Phe Asn Asn Ala Thr Thr Thr Ser Val Lys Ala Thr Leu Lys
    590                 595                 600 gtc tgg caa atg tct caa gcc ttt gtc aag gct tat ccg ttt              1871
Val Trp Gln Met Ser Gln Ala Phe Val Lys Ala Tyr Pro Phe
605                 610                 615 tagttttta tgcatctttt taagacattg ttgtttcata tgattcaagt tttatctgtg     1931
tgttatgtta agacacgcag cttaaaatag ccacatgtga gatcatttgc gtatggccgt    1991
caactatttt ttaatatgca acttcagtaa tgctatttac agtatgtttt aaggaaaaaa    2051
aaaaaaaaaa aaaaaaaaaa aa                                             2073
```

<210> SEQ ID NO 4
<211> LENGTH: 617
<212> TYPE: PRT
<213> ORGANISM: Cynara scolymus

<400> SEQUENCE: 4

```
Met Arg Thr Thr Glu Pro Gln Thr Asp Leu Glu His Ala Pro Asn His
1               5                   10                  15

Thr Pro Leu Leu Asp His Pro Glu Pro Pro Ala Ala Val Arg Asn
            20                  25                  30

Arg Leu Leu Ile Arg Val Ser Ser Ile Thr Leu Val Ser Leu Phe
        35                  40                  45

Phe Val Ser Ala Phe Leu Leu Ile Leu Leu Tyr Gln His Asp Ser Thr
    50                  55                  60

Tyr Thr Asp Asp Asn Ser Ala Pro Ser Glu Ser Ser Gln Gln Pro
65                  70                  75                  80

Ser Ala Ala Asp Arg Leu Arg Trp Glu Arg Thr Ala Phe His Phe Gln
            85                  90                  95

Pro Ala Lys Asn Phe Ile Tyr Asp Pro Asn Gly Pro Leu Phe His Met
            100                 105                 110

Gly Trp Tyr His Leu Phe Tyr Gln Tyr Asn Pro Tyr Ala Pro Phe Trp
        115                 120                 125

Gly Asn Met Thr Trp Gly His Ala Val Ser Lys Asp Met Ile Asn Trp
    130                 135                 140

Phe Glu Leu Pro Ile Ala Leu Ala Pro Thr Glu Trp Tyr Asp Ile Glu
145                 150                 155                 160

Gly Val Leu Ser Gly Ser Thr Thr Ile Leu Pro Asp Gly Arg Ile Phe
            165                 170                 175

Ala Leu Tyr Thr Gly Asn Thr Asn Asp Leu Glu Gln Leu Gln Cys Lys
        180                 185                 190

Ala Val Pro Val Asn Ala Ser Asp Pro Leu Leu Val Glu Trp Val Arg
    195                 200                 205

Tyr Asp Ala Asn Pro Ile Leu Tyr Ala Pro Ser Gly Ile Gly Leu Thr
    210                 215                 220

Asp Tyr Arg Asp Pro Ser Thr Val Trp Thr Gly Pro Asp Gly Lys His
225                 230                 235                 240
```

-continued

```
Arg Met Ile Ile Gly Thr Lys Arg Asn Thr Thr Gly Leu Val Leu Val
            245                 250                 255

Tyr His Thr Thr Asp Phe Thr Asn Tyr Val Met Leu Asp Glu Pro Leu
            260                 265                 270

His Ser Val Pro Asn Thr Asp Met Trp Glu Cys Val Asp Leu Tyr Pro
            275                 280                 285

Val Ser Thr Thr Asn Asp Ser Ala Leu Asp Val Ala Ala Tyr Gly Pro
        290                 295                 300

Gly Ile Lys His Val Leu Lys Glu Ser Trp Glu Gly His Ala Met Asp
305                 310                 315                 320

Phe Tyr Ser Ile Gly Thr Tyr Asp Ala Phe Asn Asp Lys Trp Thr Pro
                325                 330                 335

Asp Asn Pro Glu Leu Asp Val Gly Ile Gly Leu Arg Cys Asp Tyr Gly
                340                 345                 350

Arg Phe Phe Ala Ser Lys Ser Leu Tyr Asp Pro Leu Lys Lys Arg Arg
                355                 360                 365

Val Thr Trp Gly Tyr Val Ala Glu Ser Asp Ser Tyr Asp Gln Asp Val
        370                 375                 380

Ser Arg Gly Trp Ala Thr Ile Tyr Asn Val Ala Arg Thr Ile Val Leu
385                 390                 395                 400

Asp Arg Lys Thr Gly Thr His Leu Leu Gln Trp Pro Val Glu Glu Ile
                405                 410                 415

Glu Ser Leu Arg Ser Asn Gly His Glu Phe Lys Asn Ile Thr Leu Glu
                420                 425                 430

Pro Gly Ser Ile Ile Pro Leu Asp Val Gly Ser Ala Thr Gln Leu Asp
                435                 440                 445

Ile Val Ala Thr Phe Glu Val Asp Gln Glu Ala Leu Lys Ala Thr Ser
        450                 455                 460

Asp Thr Asn Asp Glu Tyr Gly Cys Thr Thr Ser Ser Gly Ala Ala Lys
465                 470                 475                 480

Gly Glu Val Leu Asp His Ser Gly Ile Ala Val Leu Ala His Gly Thr
                485                 490                 495

Leu Ser Glu Leu Thr Pro Val Tyr Phe Tyr Ile Ala Lys Asn Thr Lys
                500                 505                 510

Gly Gly Val Asp Thr His Phe Cys Thr Asp Lys Leu Arg Ser Ser Tyr
                515                 520                 525

Asp Tyr Asp Gly Glu Lys Val Val Tyr Gly Ser Thr Val Pro Val Leu
        530                 535                 540

Asp Gly Glu Glu Phe Thr Met Arg Ile Leu Val Asp His Ser Val Val
545                 550                 555                 560

Glu Gly Phe Ala Gln Gly Gly Arg Thr Val Ile Thr Ser Arg Val Tyr
                565                 570                 575

Pro Thr Lys Ala Ile Tyr Glu Ala Ala Lys Leu Phe Val Phe Asn Asn
                580                 585                 590

Ala Thr Thr Thr Ser Val Lys Ala Thr Leu Lys Val Trp Gln Met Ser
                595                 600                 605

Gln Ala Phe Val Lys Ala Tyr Pro Phe
            610                 615
```